(12) United States Patent
Tada et al.

(10) Patent No.: US 11,989,270 B2
(45) Date of Patent: May 21, 2024

(54) DETECTION DEVICE AND AUTHENTICATION METHOD

(71) Applicant: Japan Display Inc., Tokyo (JP)

(72) Inventors: Masahiro Tada, Tokyo (JP); Takashi Nakamura, Tokyo (JP); Akio Takimoto, Tokyo (JP)

(73) Assignee: Japan Display Inc., Tokyo (JP)

( * ) Notice: Subject to any disclaimer, the term of this patent is extended or adjusted under 35 U.S.C. 154(b) by 359 days.

(21) Appl. No.: 17/405,202

(22) Filed: Aug. 18, 2021

(65) Prior Publication Data

US 2021/0382973 A1 Dec. 9, 2021

Related U.S. Application Data

(63) Continuation of application No. PCT/JP2020/006374, filed on Feb. 18, 2020.

(30) Foreign Application Priority Data

Feb. 19, 2019 (JP) ................. 2019-027835

(51) Int. Cl.
| | | |
|---|---|---|
| *G06F 3/02* | (2006.01) | |
| *G06F 3/0354* | (2013.01) | |
| *G06F 21/32* | (2013.01) | |
| *G06V 40/12* | (2022.01) | |
| *G06V 40/14* | (2022.01) | |
| *G06V 40/70* | (2022.01) | |

(52) U.S. Cl.
CPC .............. *G06F 21/32* (2013.01); *G06F 3/021* (2013.01); *G06F 3/03543* (2013.01); *G06V 40/1365* (2022.01); *G06V 40/70* (2022.01); *G06V 40/14* (2022.01)

(58) Field of Classification Search
CPC ...... G06F 21/32; G06F 3/021; G06F 3/03543; G06V 40/1365; G06V 40/70; G06V 40/14
See application file for complete search history.

(56) References Cited

U.S. PATENT DOCUMENTS

| | | | |
|---|---|---|---|
| 6,337,919 B1 * | 1/2002 | Dunton | G06V 40/13 |
| | | | 345/163 |
| 2004/0022421 A1 | 2/2004 | Endoh et al. | |
| 2009/0083850 A1 * | 3/2009 | Fadell | H04L 9/3231 |
| | | | 726/19 |
| 2009/0143688 A1 | 6/2009 | Rekimoto | |

(Continued)

FOREIGN PATENT DOCUMENTS

| | | | | |
|---|---|---|---|---|
| EP | 3401767 B1 * | 9/2020 | .......... | G06F 3/0308 |
| GB | 2552721 A * | 2/2018 | .......... | G06F 1/3231 |

(Continued)

OTHER PUBLICATIONS

International Search Report in Application No. PCT/JP2020/006374, dated Apr. 21, 2020.

(Continued)

*Primary Examiner* — Darshan I Dhruv
(74) *Attorney, Agent, or Firm* — K&L Gates LLP

(57) ABSTRACT

A detection device includes an input unit configured to receive an operation of a user, and a sensor provided in the input unit and configured to detect biological information of the user when the user operates the input unit.

14 Claims, 22 Drawing Sheets

(56) References Cited

U.S. PATENT DOCUMENTS

| | | | |
|---|---|---|---|
| 2013/0308834 A1* | 11/2013 | Suzuki | G06V 40/1347 |
| | | | 382/115 |
| 2014/0121528 A1* | 5/2014 | Rekimoto | A61B 5/0059 |
| | | | 600/473 |
| 2014/0201827 A1* | 7/2014 | Okazaki | G06F 1/1684 |
| | | | 726/7 |
| 2015/0019873 A1* | 1/2015 | Hagemann | B60R 25/25 |
| | | | 713/186 |
| 2017/0076294 A1* | 3/2017 | Kojima | G06F 21/32 |
| 2017/0118206 A1* | 4/2017 | Liu | G06F 21/32 |
| 2017/0357979 A1* | 12/2017 | Khurana | G07F 7/0846 |
| 2017/0374065 A1* | 12/2017 | Shtraym | G06F 21/32 |
| 2018/0150671 A1* | 5/2018 | Choo | G06F 3/0421 |
| 2020/0050342 A1* | 2/2020 | Lee | G06F 17/16 |
| 2020/0065470 A1* | 2/2020 | Van Os | G06F 3/0488 |

FOREIGN PATENT DOCUMENTS

| | | |
|---|---|---|
| JP | 2004062826 A | 2/2004 |
| JP | 2009140019 A | 6/2009 |
| JP | 2017117477 A | 6/2017 |
| JP | 2017151508 A | 8/2017 |

OTHER PUBLICATIONS

Japanese Office Action dated Dec. 6, 2022 in corresponding Japanese Application No. 2019-027835.

* cited by examiner

DETECTION DEVICE AND AUTHENTICATION METHOD

CROSS-REFERENCE TO RELATED APPLICATION

This application is a continuation of International Patent Application No. PCT/JP2020/006374 filed on Feb. 18, 2020, incorporated herein by reference, and which claims the benefit of priority from Japanese Patent Application No. 2019-027835 filed on Feb. 19, 2019, incorporated herein by reference.

BACKGROUND

1. Technical Field

The present disclosure relates to a detection device and an authentication method.

2. Description of the Related Art

An authentication system can be mounted on an electronic device in order to restrict access to the electronic device. For example, Japanese Patent Application Laid-open Publication No. 2017-117477 (JP-A-2017-117477) discloses that a display for authentication is displayed to a user. JP-A-2017-117477 also discloses that a sensor for the authentication is provided in a keyboard of the electronic device.

When the display for the authentication is displayed as in JP-A-2017-117477, the user needs to perform an operation only for the authentication in order to operate the electronic device and can be required to take labor and time. Accordingly, reduction in the labor and time for the authentication has been desired.

The present disclosure has been made in view of the above-mentioned problem, and an object thereof is to provide a detection device and an authentication method capable of reducing labor and time for authentication.

SUMMARY

A detection device according to the present disclosure includes an input device configured to receive an operation of a user, and a sensor provided in the input device and configured to detect biological information of the user when the user operates the input device.

DETAILED DESCRIPTION

Figure 1:
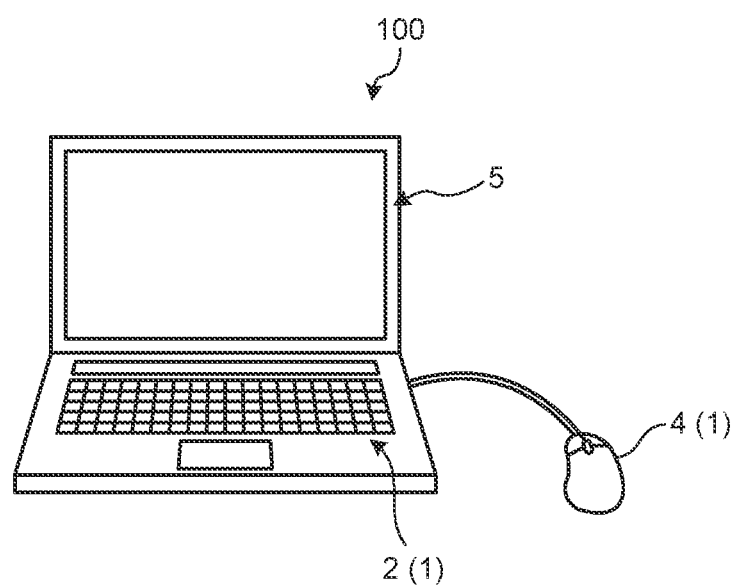
FIG. 1 is a schematic view of a detection device according to a first embodiment.

Modes for carrying out the disclosure (embodiments) will be described in detail with reference to the drawings. Contents described in the following embodiments do not limit the present disclosure. Components described below include those that can be easily assumed by those skilled in the art and substantially the same components. Furthermore, the components described below can be appropriately combined. What is disclosed herein is merely an example, and it is needless to say that appropriate modifications within the gist of the disclosure at which those skilled in the art can easily arrive are encompassed in the range of the present disclosure. In the drawings, widths, thicknesses, shapes, and the like of the components can be schematically illustrated in comparison with actual modes for clearer explanation. They are, however, merely examples and do not limit interpretation of the present disclosure. In the present specification and the drawings, the same reference numerals denote components equivalent to those described before with reference to the drawing that has been already referred, and detail explanation thereof can be appropriately omitted.

First Embodiment

Overall Configuration

FIG. 1 is a schematic view of a detection device according to a first embodiment. A detection device 100 in the first embodiment is an electronic apparatus that receives a user operation through an input unit 1 and executes a predetermined operation (processing) based on the user operation input to the input unit 1. The detection device 100 includes, in the input unit 1, sensors 10 (see FIG. 2) configured to detect biological information of a user when the user operates the input unit 1.

As illustrated in FIG. 1, the detection device 100 in the first embodiment is a computer and includes the input unit 1, a display unit 5, and a controller 6 and a storage unit 8, which will be described later. The input unit 1 is an input device configured to receive the user operation and includes a keyboard 2 and a mouse 4 in the embodiment. The display unit 5 as an output unit is a display device configured to display an image. The detection device 100 in FIG. 1 is a lap-top computer but is not limited thereto and may be a desktop computer.

Figure 2:
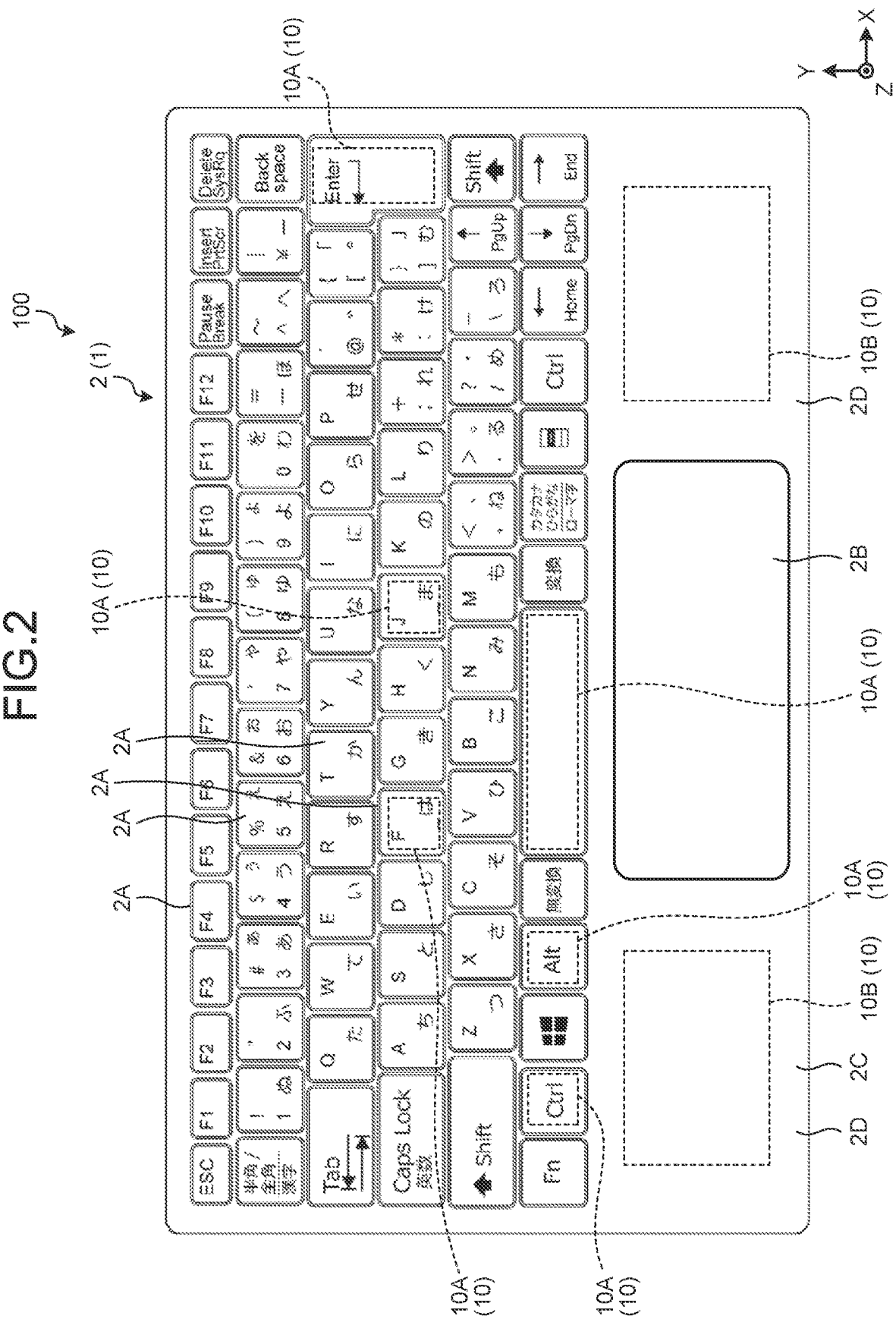
FIG. 2 is a view illustrating an example of a keyboard according to the first embodiment.

FIG. 2 is a view illustrating an example of the keyboard according to the first embodiment. As illustrated in FIG. 2, the keyboard 2 includes a plurality of buttons (keys) 2A, an operation unit 2B, and a housing 2C. The housing 2C is a main body portion of the keyboard 2 and includes the buttons 2A and the operation unit 2B on the surface thereof. Hereinafter, one direction along the surfaces of the buttons 2A is a direction X, and one direction along the surfaces of the buttons 2A and intersecting with the direction X is a direction Y. To be more specific, the direction Y is orthogonal to the direction X in the embodiment. One direction orthogonal to the surfaces of the buttons 2A, that is, one direction orthogonal to the directions X and Y is a Z direction. The direction Z is a direction toward the side of the surfaces of the buttons 2A.

The buttons 2A are physical buttons and are arrayed in the directions X and Y in a matrix with a row-column configuration. The operation unit 2B is an operation panel for moving a cursor that is displayed on the display unit 5 when the user operates it so as to trace the surface of the operation unit 2B. The operation unit 2B is located on the opposite direction side to the buttons 2A in the direction Y. The direction Y is directed away from the user.

The detection device 100 in the first embodiment includes the sensors 10 configured to detect the biological information of the user in the thus configured keyboard 2. Although a plurality of sensors 10 are provided in the keyboard 2, the number of sensors 10 may be set to any number and may be one.

To be more specific, the detection device 100 according to the first embodiment includes, as the sensors 10, first sensors 10A and second sensors 10B. The first sensors 10A are provided in the buttons 2A. In the example of FIG. 2, the first sensors 10A are provided in some of the buttons 2A. The first sensors 10A are provided in, for example, the button 2A for inputting F and the button 2A for inputting J on which the right and left forefingers are placed for a long time, the button 2A for inputting a space on which the thumbs are placed for a long time, and the button 2A for inputting enter, a Control button, and an Alt button that are frequently pressed. The buttons 2A in which the first sensors 10A are provided are, however, not limited thereto and any button may be set. The first sensors 10A may be provided in all the buttons 2A, for example.

The second sensors 10B are provided in regions 2D. The regions 2D are on the side closer to the user than the buttons 2A are, that is, on the opposite side to the buttons 2A in the direction Y, on the surface of the housing 2C. To be more specific, the regions 2D are located on both sides of the operation unit 2B, that is, on one side of the operation unit 2B in the direction X and the other side of the operation unit 2B in the direction opposite to the direction X. That is to say, the second sensors 10B are provided at places where the user brings the palms of his(her) hands into contact with the keyboard 2 when operating the keyboard 2. The positions at which the second sensors 10B are provided are, however, not limited thereto. The second sensors 10B may not be provided. The first sensors 10A may be incorporated in the operation unit 2B.

The first sensors 10A are sensors configured to acquire the biological information of the user, and detect the fingerprints of the user and the blood vessel patterns of the user in the first embodiment. The blood vessel pattern indicates an image of the blood vessel, and is a vein pattern in the embodiment. The second sensors 10B are sensors configured to detect the blood vessel patterns of the user's hands. The second sensors 10B may be configured to be capable of detecting the fingerprints, palm prints, or the like of the user. Although the sensors 10 detect the fingerprints and the blood vessel patterns as the biological information of the user, they may detect at least one of the fingerprints and the blood vessel patterns. The sensors 10 may detect other biological information (for example, pulses or pulse waves) than the fingerprints and the blood vessel patterns. The configuration of the sensors 10 will be described later.

Figure 3:
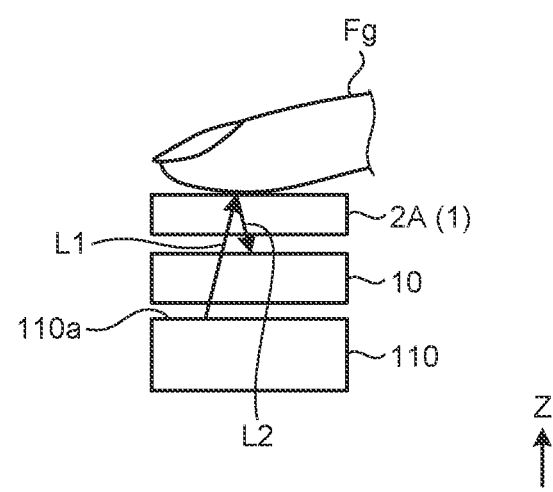
FIG. 3 is a cross-sectional view illustrating the schematic cross-sectional configuration of the detection device according to the first embodiment.

FIG. 3 is a cross-sectional view illustrating the schematic cross-sectional configuration of the detection device according to the first embodiment. FIG. 3 illustrates the multilayered configuration of the input unit 1, the sensor 10, and a light source unit 110. The light source unit 110, the sensor 10, and the input unit 1 are aligned in this order toward the direction Z. Although the button 2A is illustrated as the input unit 1 in the example of FIG. 3, a similar multilayered configuration is employed also when the sensor 10 is provided in another input unit 1 such as the mouse 4. A similar multilayered configuration is employed also when the sensor 10 (second sensor 10B) is provided in the region 2D.

The light source unit 110 has a light emission surface 110a for emitting light and emits light L1 toward the sensor 10 of the detection device 100 from the light emission surface 110a. The light source unit 110 is backlight. The light source unit 110 may include, as a light source, a light emitting diode (LED) emitting light in a predetermined color, for example. A micro LED mounted on an insulating substrate 21 (see FIG. 9), which will be described later, may be used as the light source. The light source unit 110 may be what is called side light-type backlight including a light guide plate provided at a position corresponding to the sensor 10 and a plurality of light sources aligned on one end or both ends of the light guide plate. The light source unit 110 may be what is called direct backlight including a light source (for example, LED) provided just under the sensor 10. The light source unit 110 is not limited to the backlight and may be provided on a lateral side of the detection device 100 and may emit the light L1 from the lateral side of a finger Fg of the user. Detection may be performed with natural light without using the light source.

The sensor 10 is provided so as to face the light emission surface 110a of the light source unit 110. In other words, the sensor 10 is provided between the light source unit 110 and the input unit 1. Light L1 emitted from the light source unit 110 passes through the sensor 10 and the input unit 1. The sensor 10 is, for example, a light reflective biological information sensor and can detect irregularities (for example, the fingerprint) on the surface of the finger Fg, the palm of the hand, or the like by detecting light L2 reflected by an interface between the input unit 1 and the air. The sensor 10 may detect the blood vessel pattern or another biological information by detecting the light L2 reflected in the inside of the finger Fg or the palm of the hand. The color of the light L1 from the light source unit 110 may be different depending on a detection target. For example, the light source unit 110 can emit light L1 in blue or green in the case of detection of the fingerprint, and the light source unit 110 can emit light L1 of infrared light in the case of detection of the blood vessel pattern.

The input unit 1 to which the sensor 10 is provided is configured so as to cover the sensor 10 and the light source unit 110. In this case, the input unit 1 is formed by a member having a light transmitting property and is preferably made of, for example, transparent resin. The input unit 1 to which no sensor 10 is provided may not have the light transmitting property. Although the light source unit 110 is provided for each sensor 10 in the embodiment, one light source unit 110 common to the sensors 10 may be provided.

Figure 4:
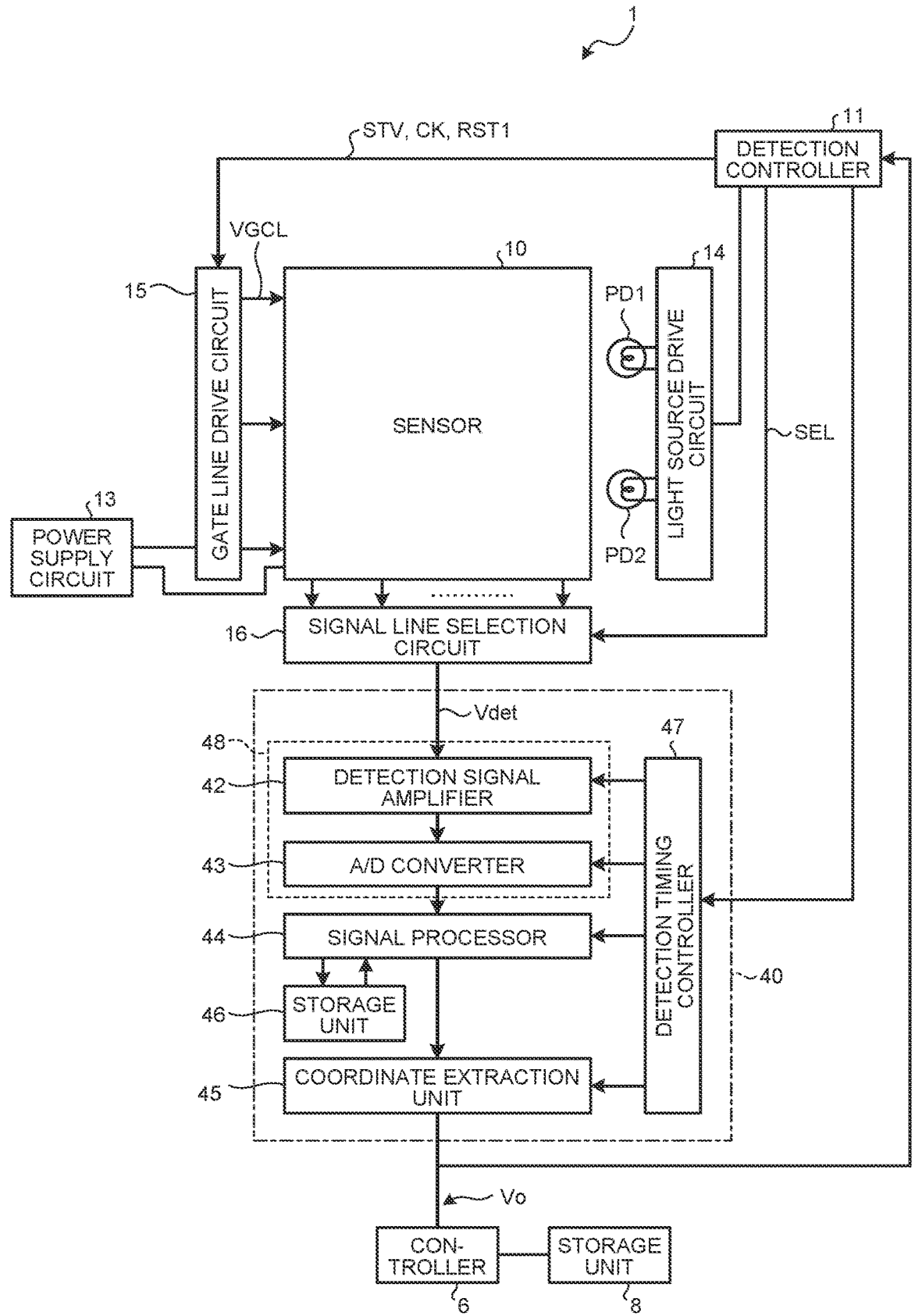
FIG. 4 is a block diagram illustrating an example of the configuration of the detection device according to the first embodiment.

FIG. 4 is a block diagram illustrating an example of the configuration of the detection device in the first embodiment. As illustrated in FIG. 4, the detection device 100 includes the controller 6, the storage unit 8, the sensor 10, a detection controller 11, a power supply circuit 13, a gate line drive circuit 15, a signal line selection circuit 16, and a detector 40. The controller 6 is an arithmetic device that is mounted on the detection device 100, that is, a central processing unit (CPU). The controller 6 executes various pieces of processing by reading a computer program from the storage unit 8, for example. The storage unit 8 is a memory storing therein operation contents performed by the controller 6, information of the computer program, and the like and includes at least one of a random-access memory (RAM), a read-only memory (ROM), and an external storage device such as a hard disk drive (HDD). The above-mentioned controller 6 and storage unit 8 can also have some or all of the functions of a signal processor 44, a storage unit 46, and a coordinate extraction unit 45 included in the detector 40.

The sensor 10 is an optical sensor including at least one of a first photodiode PD1 and a second photodiode PD2 as a photoelectric conversion element. The first photodiode PD1 and the second photodiode PD2 included in the sensor 10 output, as detection signals Vdet, electric signals corresponding to emitted light to the signal line selection circuit 16. The sensor 10 performs detection in accordance with gate drive signals VGCL supplied from the gate line drive circuit 15.

The detection controller 11 is a circuit that supplies control signals to the gate line drive circuit 15, the signal line selection circuit 16, and the detector 40 to control operations thereof. The detection controller 11 supplies, to the gate line drive circuit 15, various control signals such as a start signal STV, a clock signal CK, and a reset signal RST1. The detection controller 11 supplies, to the signal line selection circuit 16, various control signals such as selection signals SEL. The power supply circuit 13 is a circuit provided in the detection device 100 and supplies voltage signals such as a power supply signal SVS (see FIG. 7) to the sensor 10, the gate line drive circuit 15, and the like.

The gate line drive circuit 15 drives a plurality of gate lines GCL (see FIG. 5) based on various control signals. The gate line drive circuit 15 selects the gate lines GCL sequentially or simultaneously and supplies the gate drive signals VGCL to the selected gate lines GCL. The gate line drive circuit 15 thereby selects a plurality of first photodiodes PD1 and a plurality of second photodiodes PD2 coupled to the gate lines GCL.

The signal line selection circuit 16 is a switch circuit that selects a plurality of signal lines SGL (see FIG. 5) sequentially or simultaneously. The signal line selection circuit 16 couples the selected signal lines SGL and an analog front-end circuit (AFE) 48, which will be described later, as a detection circuit based on the selection signals SEL supplied from the detection controller 11. The signal line selection circuit 16 thereby outputs the detection signals Vdet of the first photodiodes PD1 and the second photodiodes PD2 to the detector 40. The signal line selection circuit 16 is, for example, a multiplexer. The detection device 100 may include a light source drive circuit 14. The light source drive circuit 14 drives the first photodiodes PD1 and the second photodiodes PD2 based on signals from the detection controller 11. The light source drive circuit 14 may drive the light source unit 110 to cause the light source unit 110 to emit light L1 based on the signal from the detection controller 11.

The detector 40 is a circuit including the AFE 48, the signal processor 44, the coordinate extraction unit 45, the storage unit 46, and a detection timing controller 47. The detection timing controller 47 controls such that the AFE 48, the signal processor 44, and the coordinate extraction unit 45 operate synchronously based on the control signals supplied from the detection controller 11.

The AFE 48 is a signal processing circuit having functions of at least a detection signal amplifier 42 and an A/D converter 43. The detection signal amplifier 42 amplifies the detection signals Vdet output from the sensor 10 through the signal line selection circuit 16. The A/D converter 43 converts, into digital signals, analog signals output from the detection signal amplifier 42, that is, the amplified detection signals Vdet.

The signal processor 44 is a logical circuit that detects a predetermined physical quantity input to the sensor 10 based on the output signals of the AFE 48, that is, the detection signals Vdet converted into the digital signals. In the case where the signal processor 44 receives an instruction from the controller 6 when the finger Fg or the palm of the hand is brought into contact with or close to the input unit 1, it can detect the irregularities (that is, the fingerprint) on the surface of the finger Fg or the blood vessel pattern of the finger Fg or the palm of the hand based on the detection signals Vdet from the AFE 48. Hereinafter, unless otherwise specified, when the finger Fg or the palm of the hand is brought into contact with the input unit 1 or when the finger Fg or the palm of the hand is located at a position so close that the biological information can be detected therefrom, an expression "proximity" is used.

The storage unit 46 temporarily stores therein the signals subjected to the arithmetic operation by the signal processor 44. The storage unit 46 may be, for example, a random-access memory (RAM) or a register circuit.

The coordinate extraction unit 45 is a logical circuit that calculates detection coordinates of the irregularities on the surface of the finger Fg or the like when the signal processor 44 detects proximity of the finger Fg or the palm of the hand. The coordinate extraction unit 45 generates two-dimensional information indicating a shape of the irregularities (that is, the fingerprint) on the surface of the finger Fg or a shape of the blood vessel pattern of the finger Fg or the palm of the hand by combining the detection signals Vdet output from the first photodiodes PD1 and the second photodiodes PD2 of the sensors 10. It can be regarded that the two-dimensional information is the biological information of the user. The coordinate extraction unit 45 may output the detection signals Vdet as sensor output Vo without calculating the detection coordinates. In this case, the detection signals Vdet may be referred to as the biological information of the user.

The controller 6 acquires the two-dimensional information generated by the coordinate extraction unit 45, that is, the biological information of the user that the sensor 10 has detected. The controller 6 reads, from the storage unit 8, previously stored two-dimensional information, that is, reference biological information as biological information being a reference. The controller 6 collates the reference biological information and the biological information of the user that the sensor 10 has detected and determines whether the biological information of the user that the sensor 10 has detected matches the reference biological information. That is to say, the controller 6 performs user authentication using the biological information of the user that the sensor 10 has detected. When the biological information of the user that the sensor 10 has detected matches the reference biological information, the controller 6 determines that authentication is affirmative and controls the detection device 100 to execute a predetermined function. The predetermined function is, for example, a function that the user requests to execute from the detection device 100, and examples thereof include activation of the computer program (application) of the detection device 100 and access to a web site. When the biological information of the user that the sensor 10 has detected does not match the reference biological information, the controller 6 determines that the authentication is negative and does not execute the predetermined function. When the coordinate extraction unit 45 does not calculate the detection coordinates, the controller 6 generates the two-dimensional information indicating the shape of the irregularities (that is, the fingerprint) on the surface of the finger Fg or the shape of the blood vessel pattern of the finger Fg or the palm of the hand based on the detection signals Vdet.

Configuration of First Sensor

Figure 5:
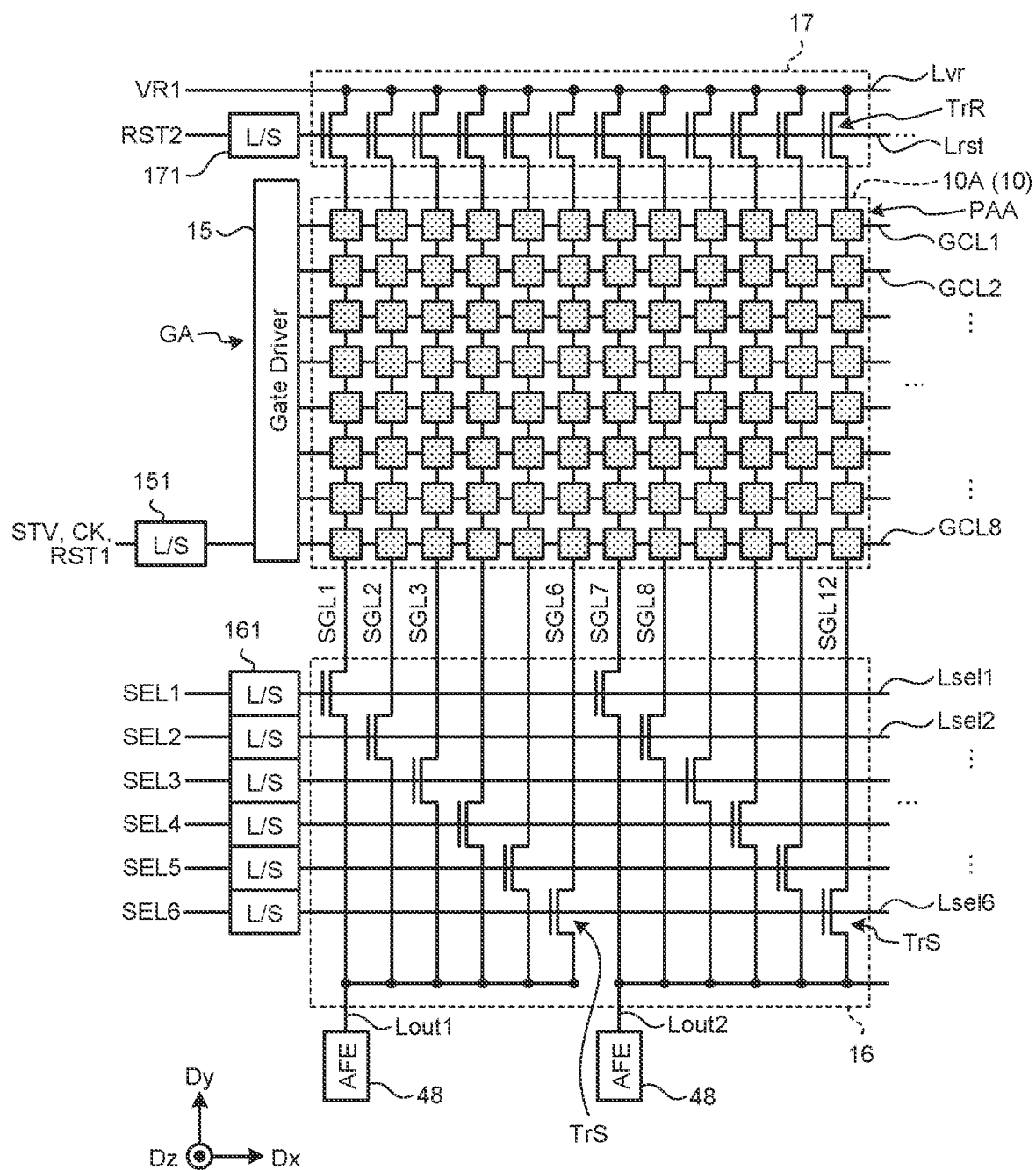
FIG. 5 is a circuit diagram illustrating the detection device according to the first embodiment.
Figure 6:
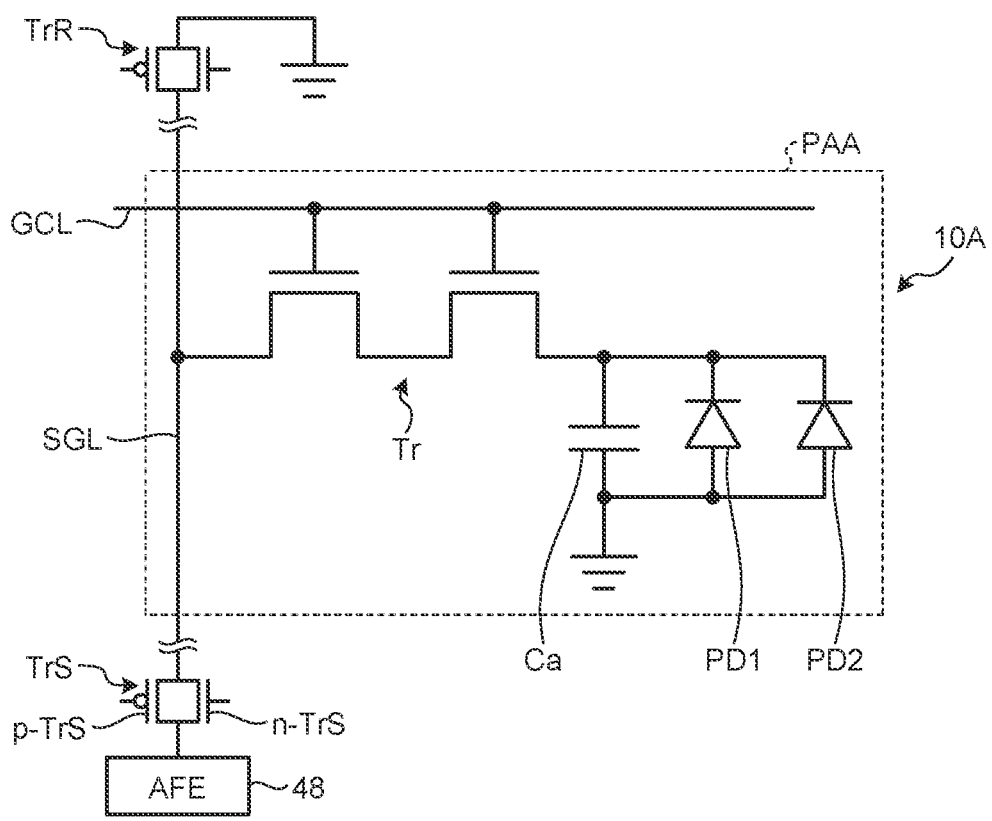
FIG. 6 is an equivalent circuit diagram illustrating a first sensor in the first embodiment.
Figure 7:
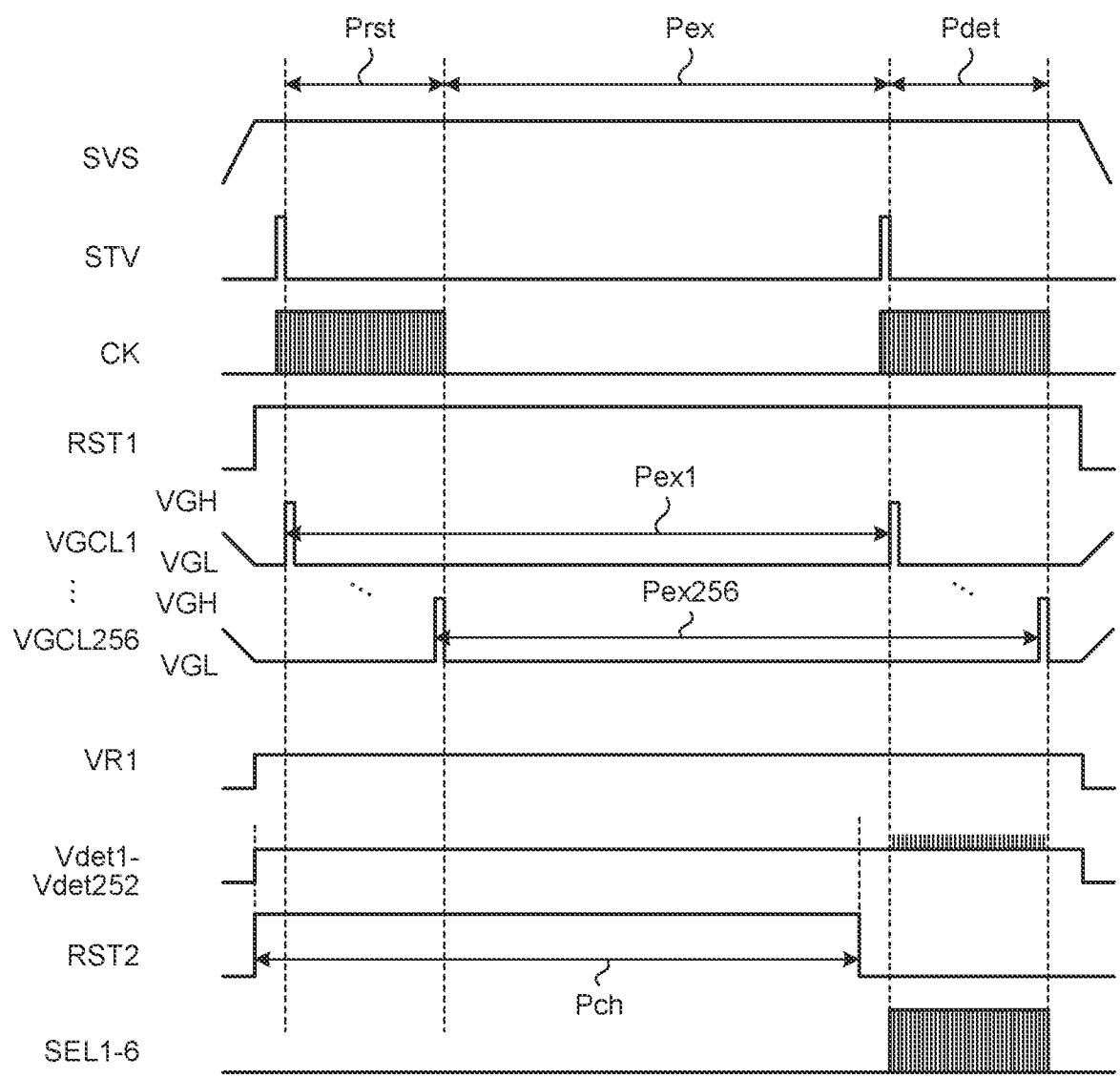
FIG. 7 is a timing waveform chart illustrating an example of operations of the detection device according to the first embodiment.

Next, a circuit configuration example and an operation example of the detection device 100, more specifically, the configuration of the first sensor 10A will be described. FIG. 5 is a circuit diagram illustrating the detection device according to the first embodiment. FIG. 5 illustrates the circuit diagram including the first sensor 10A of the sensors 10. A circuit diagram including the second sensor 10B is also similar to that illustrated in FIG. 5, and description of common parts is therefore omitted. FIG. 6 is an equivalent circuit diagram illustrating the first sensor according to the first embodiment. FIG. 7 is a timing waveform chart illustrating an example of operations of the detection device according to the first embodiment.

As illustrated in FIG. 5, the first sensor 10A has a plurality of partial detection regions PAA arrayed in a matrix with a row-column configuration. As illustrated in FIG. 6, each of the partial detection regions PAA of the first sensor 10A includes the first photodiode PD1 and the second photodiode PD2, a capacitor element Ca, and a first switching element Tr. The first switching element Tr is provided for the first photodiode PD1 and the second photodiode PD2. The first switching element Tr is formed by a thin film transistor and, in this example, is formed by an n-channel thin film transistor (TFT).

The gate of the first switching element Tr is coupled to the gate line GCL. The source of the first switching element Tr is coupled to the signal line SGL. The drain of the first switching element Tr is coupled to a cathode electrode 34 of the first photodiode PD1, a cathode electrode 54 of the second photodiode PD2, and one end of the capacitor element Ca. An anode electrode 35 of the first photodiode PD1, an anode electrode 55 of the second photodiode PD2, and the other end of the capacitor element Ca are coupled to a reference potential, for example, a ground potential. The first photodiode PD1 and the second photodiode PD2 are thus coupled in parallel to the first switching element Tr in the same direction.

A third switching element TrS and a fourth switching element TrR are coupled to the signal line SGL. The third switching element TrS and the fourth switching element TrR are elements configuring the drive circuit that drives the first switching element Tr. In the embodiment, the drive circuit includes the gate line drive circuit 15, the signal line selection circuit 16, and a reset circuit 17 provided in a peripheral region that does not overlap with the partial detection region PAA. The third switching element TrS is configured by, for example, a CMOS (complementary MOS) transistor provided by combining a p-channel transistor p-TrS and an n-channel transistor n-TrS. The fourth switching element TrR is also configured by the CMOS transistor similarly.

When the fourth switching elements TrR of the reset circuit 17 are turned ON, a reference signal VR1 to be an initial potential of the capacitor elements Ca is supplied to the capacitor elements Ca from the power supply circuit 13. The capacitor elements Ca are thereby reset. When light is emitted to the partial detection region PAA, electric current corresponding to light amounts flows through the first photodiodes PD1 and the second photodiodes PD2, and electric charges are thereby accumulated in the capacitor elements Ca. When the first switching elements Tr are turned ON, current flows through the signal lines SGL in response to the electric charges accumulated in the capacitor elements Ca. The signal lines SGL are coupled to the AFEs 48 through the third switching elements TrS of the signal line selection circuit 16. The detection device 100 can thereby detect signals corresponding to the amounts of light emitted to the first photodiodes PD1 and the second photodiodes PD2 for each partial detection region PAA.

As illustrated in FIG. 5, the gate lines GCL extend in a first direction Dx and are coupled to the partial detection regions PAA aligned in the first direction Dx. The gate lines GCL1, GCL2, . . . , and GCL8 are aligned in a second direction Dy, and each of them is coupled to the gate line drive circuit 15. In the following description, when the gate lines GCL1, GCL2, . . . , and GCL8 need not be distinguished from one another for description, they are simply expressed as the gate lines GCL. The number of gate lines GCL is eight but this is merely an example, and equal to or more than eight gate lines GCL may be aligned.

The first direction Dx is one direction in a plane parallel with the insulating substrate 21 of the sensor 10 and is, for example, a direction parallel with the gate lines GCL. The second direction Dy is one direction in the plane parallel with the insulating substrate 21 and is a direction orthogonal to the first direction Dx. The second direction Dy may not be orthogonal to but intersect with the first direction Dx. A third direction Dz is orthogonal to the first direction Dx and the second direction Dy and is perpendicular to the insulating substrate 21. The third direction Dz matches the above-mentioned direction Z.

The signal lines SGL extend in the second direction Dy and are coupled to the partial detection regions PAA aligned in the second direction Dy. The signal lines SGL1, SGL2, ..., and SGL12 are aligned in the first direction Dx, and each of them is coupled to the signal line selection circuit 16 and the reset circuit 17. The number of signal lines SGL is 12 but is merely an example, and equal to or more than 12 signal lines SGL may be aligned. In FIG. 5, the first sensor 10A is provided between the signal line selection circuit 16 and the reset circuit 17. The arrangement is not limited thereto, and the signal line selection circuit 16 and the reset circuit 17 may be coupled to each of the end portions of the signal lines SGL in the same direction.

The gate line drive circuit 15 receives various control signals such as the start signal STV, the clock signal CK, and the reset signal RST1 through a level shifter 151. The gate line drive circuit 15 includes a plurality of second switching elements TrG (not illustrated). The gate line drive circuit 15 selects the gate lines GCL1, GCL2, ..., and GCL8 sequentially in a time division manner through operations by the second switching elements TrG. The gate line drive circuit 15 supplies the gate drive signals VGCL to the first switching elements Tr through the selected gate lines GCL. The partial detection regions PAA aligned in the first direction Dx are thereby selected as the detection targets.

The signal line selection circuit 16 includes a plurality of selection signal lines Lsel, a plurality of output signal lines Lout, and the third switching elements TrS. The third switching elements TrS are provided so as to respectively correspond to the signal lines SGL. Six signal lines SGL1, SGL2, ..., and SGL6 are coupled to a common output signal line Lout1. Six signal lines SGL7, SGL8, ..., and SGL12 are coupled to a common output signal line Lout2. The output signal lines Lout1 and lout2 are respectively coupled to the AFEs 48.

The signal lines SGL1, SGL2, ..., and SGL6 are set as a first signal line block, and the signal lines SGL7, SGL8, ..., and SGL12 are set as a second signal line block. The selection signal lines Lsel are respectively coupled to the gates of the third switching elements TrS included in one signal line block. One selection signal line Lsel is coupled to the gates of the third switching element TrS in the signal line blocks. To be specific, the selection signal lines Lsel1, Lsel2, ..., and Lsel6 are coupled to the third switching elements TrS corresponding to the signal lines SGL1, SGL2, ..., and SGL6. The selection signal line Lsel1 is coupled to the third switching element TrS corresponding to the signal line SGL1 and the third switching element TrS corresponding to the signal line SGL7. The selection signal line Lsel2 is coupled to the third switching element TrS corresponding to the signal line SGL2 and the third switching element TrS corresponding to the signal line SGL8.

The detection controller 11 (see FIG. 4) supplies the selection signals SEL to the selection signal lines Lsel sequentially through level shifters 161. The signal line selection circuit 16 thereby selects the signal lines SGL in one signal line block sequentially in a time division manner through operations by the third switching elements TrS. The signal line selection circuit 16 simultaneously selects the signal lines SGL one by one in the signal line blocks. With the above-mentioned configuration, the detection device 100 can reduce the number of integrated circuits (ICs) including the AFEs 48 or the number of terminals of the ICs.

As illustrated in FIG. 5, the reset circuit 17 includes a reference signal line Lvr, a reset signal line Lrst, and the fourth switching elements TrR. The fourth switching elements TrR are provided so as to correspond to the signal lines SGL. The reference signal line Lvr is coupled to ones of the sources and drains of the fourth switching elements TrR. The reset signal line Lrst is coupled to the gates of the fourth switching elements TrR.

The detection controller 11 (see FIG. 4) supplies a reset signal RST2 to the reset signal line Lrst through a level shifter 171. The fourth switching elements TrR are thereby turned ON, and the signal lines SGL are electrically coupled to the reference signal line Lvr. The power supply circuit 13 (see FIG. 4) supplies the reference signal VR1 to the reference signal line Lvr. The reference signal VR1 is thereby supplied to the capacitor elements Ca included in the partial detection regions PAA.

Hereinbefore, the circuit configuration of the circuits coupled to the first sensor 10A has been described. In the above description, circuits including one detection controller 11, one gate line drive circuit 15, one signal line selection circuit 16, one reset circuit 17, and one detector 40 are provided for one first sensor 10A. Alternatively, one common circuit may be provided for the first sensors 10A. That is to say, in this case, the circuits including one gate line drive circuit 15, one signal line selection circuit 16, one reset circuit 17, and one detector 40 may be provided for the first sensors 10A.

Next, an example of operations of the detection device 100 will be described. As illustrated in FIG. 7, the detection device 100 has a reset period Prst, an exposure period Pex, and a reading period Pdet. The power supply circuit 13 supplies a power supply signal SVS to the first photodiodes PD1 and the second photodiodes PD2 over the reset period Prst, the exposure period Pex, and the reading period Pdet. The detection controller 11 supplies the reference signal VR1 of a high-level voltage signal and the reset signal RST2 to the reset circuit 17 at the time before the reset period Prst is started. The detection controller 11 supplies the start signal STV to the gate line drive circuit 15, and the reset period Prst is started.

The gate line drive circuit 15 selects the gate lines GCL sequentially based on the start signal STV, the clock signal CK, and the reset signal RST1 in the reset period Prst. The gate line drive circuit 15 supplies the gate drive signals VGCL to the gate lines GCL sequentially. The gate drive signals VGCL have pulse-like waveforms having high-level voltages VGH and low-level voltages VGL. In the example of FIG. 7, 256 gate lines GCL are provided, and gate drive signals VGCL1, ..., and VGCL256 are supplied to the gate lines GCL sequentially.

In the reset period Prst, the capacitor elements Ca in all the partial detection regions PAA are thereby electrically coupled to the signal lines SGL sequentially, and the reference signal VR1 is supplied thereto. As a result, the capacitance of the capacitor elements Ca is reset.

The exposure period Pex is started after the gate drive signal VGCL256 is supplied to the gate line GCL. Start timings and end timings of actual exposure periods Pex1, ..., and Pex256 in the partial detection regions PAA corresponding to the respective gate lines GCL are different. Each of the exposure periods Pex1, ..., and Pex256 is started at a timing at which the gate drive signal VGCL is changed to the low-level voltage VGL from the high-level voltage VGH in the reset period Prst. Each of the exposure periods Pex1, ..., and Pex256 is ended at a timing at which the gate drive signal VGCL is changed to the high-level voltage VGH from the low-level voltage VGL in the reading period Pdet. The lengths of the exposure time of the exposure periods Pex1, ..., and Pex256 are equal.

In the exposure period Pex, the current flows correspondingly to light emitted to the first photodiodes PD1 and the second photodiodes PD2 in the partial detection regions PAA. As a result, the electric charges are accumulated in the capacitor elements Ca.

The detection controller 11 sets the reset signal RST2 to a low-level voltage at a timing before the reading period Pdet is started. The operation of the reset circuit 17 is thereby stopped. In the reading period Pdet, the gate line drive circuit 15 supplies the gate drive signals VGCL1, . . . , and VGCL256 sequentially to the gate lines GCL, similarly to the reset period Prst.

The detection controller 11 supplies the selection signals SEL1, . . . , and SEL6 to the signal line selection circuit 16 sequentially in a period in which the gate drive signal VGCL1 is at the high-level voltage VGH, for example. The signal lines SGL in the partial detection region PAA selected by the gate drive signal VGCL1 are thereby coupled to the AFEs 48 sequentially or simultaneously. As a result, the detection signals Vdet are supplied to the AFEs 48. Similarly, the signal line selection circuit 16 selects the signal lines SGL sequentially, every period in which each gate drive signal VGCL becomes the high-level voltage VGH. The detection device 100 can thereby output the detection signals Vdet in all the partial detection regions PAA to the AFEs 48 in the reading period Pdet.

The detection device 100 may repeat the reset period Prst, the exposure period Pex, and the reading period Pdet to perform detection. Alternatively, the detection device 100 may start the detection operation at a timing at which proximity of the finger Fg or the like to the input unit 1 is detected.

Figure 8:
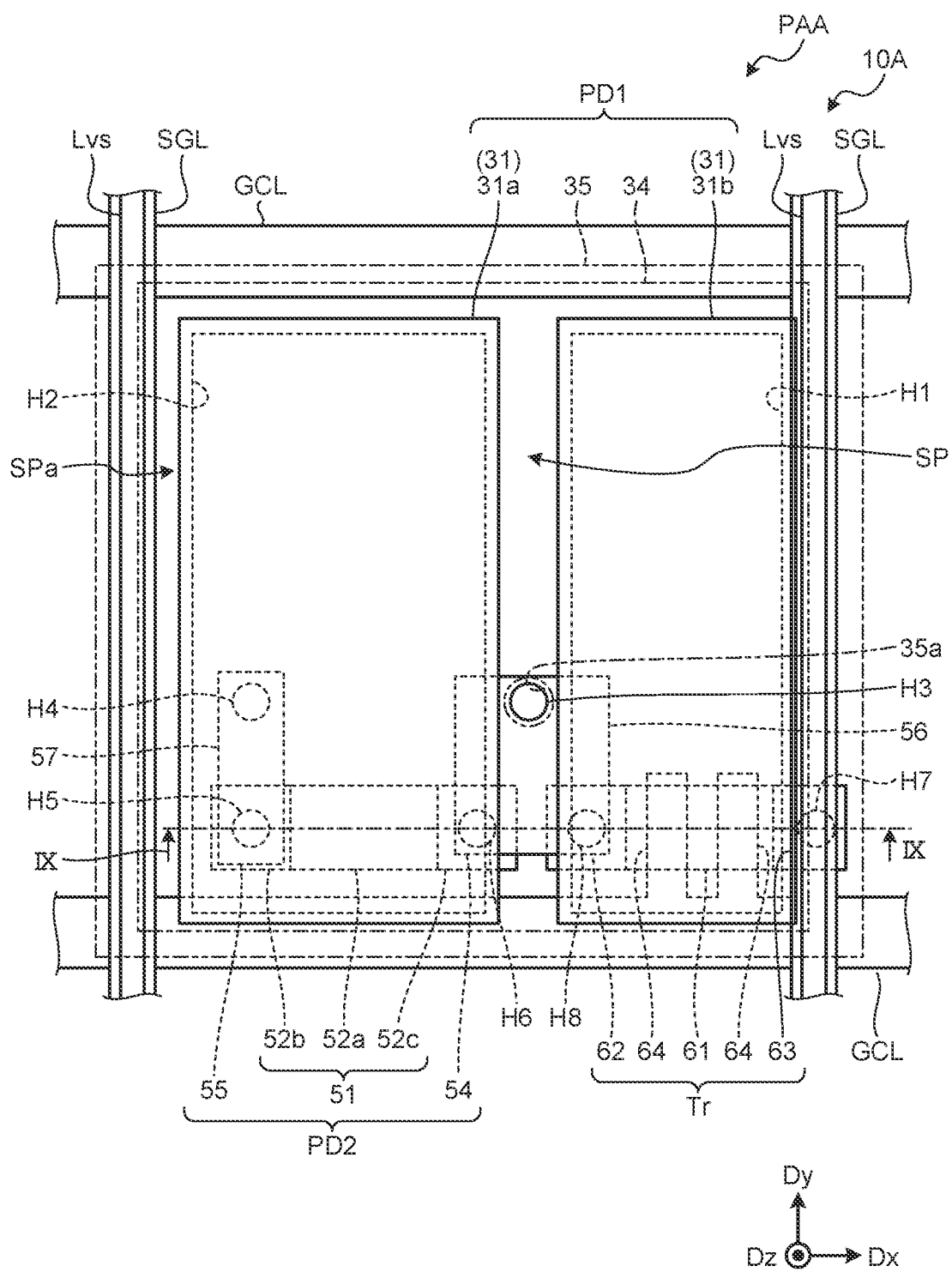
FIG. 8 is a plan view schematically illustrating a partial detection region of the first sensor according to the first embodiment.
Figure 9:
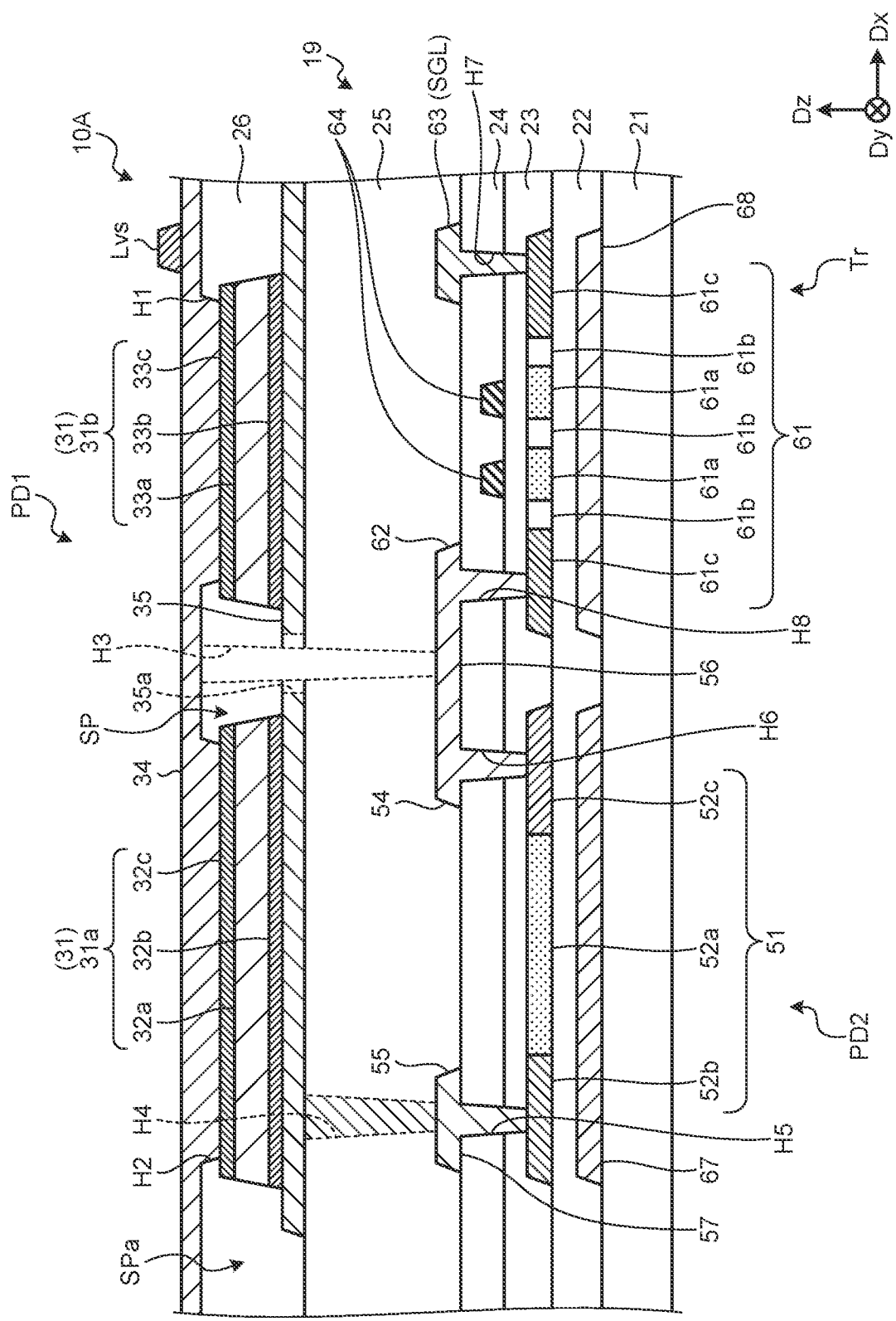
FIG. 9 is a cross-sectional view cut along line IX-IX in FIG. 8.

Next, the specific configuration of the first sensor 10A will be described. FIG. 8 is a plan view schematically illustrating the partial detection region of the first sensor according to the first embodiment. FIG. 9 is a cross-sectional view cut along line IX-IX in FIG. 8. In FIG. 8, the cathode electrode 34 and the anode electrode 35 are indicated by chain double-dashed line for making the drawing easy to view.

In the following description, the direction toward the first photodiode PD1 from the insulating substrate 21 in the direction perpendicular to the surface of the insulating substrate 21, that is, the third direction Dz side is an "upper side" or simply "upward". The direction toward the insulating substrate 21 from the first photodiode PD1, that is, the opposite direction to the third direction Dz is a "lower side" or simply "downward". The expression "when seen from above" indicates the case when seen from the direction perpendicular to the surface of the insulating substrate 21.

As illustrated in FIG. 8, the partial detection region PAA of the first sensor 10A is a region surrounded by the gate lines GCL and the signal lines SGL. The first photodiode PD1, the second photodiode PD2, and the first switching element Tr are provided in the partial detection region PAA, that is, the region surrounded by the gate lines GCL and the signal lines SGL. The first photodiode PD1 and the second photodiode PD2 are, for example, positive intrinsic negative diode (PIN)-type photodiodes.

The photodiode PD1 includes a first semiconductor layer 31, the cathode electrode 34, and the anode electrode 35. The first semiconductor layer 31 includes a first partial semiconductor layer 31a and a second partial semiconductor layer 31b. The first partial semiconductor layer 31a and the second partial semiconductor layer 31b of the first photodiode PD1 are made of amorphous silicon (a-Si). The first partial semiconductor layer 31a and the second partial semiconductor layer 31b are provided so as to be adjacent to each other with a space SP interposed therebetween in the first direction Dx. The cathode electrode 34 and the anode electrode 35 are provided continuously over a region overlapping with the first partial semiconductor layer 31a, the second partial semiconductor layer 31b, and the space SP. In the following description, when the first partial semiconductor layer 31a and the second partial semiconductor layer 31b need not be distinguished from each other for description, they are simply expressed as the first semiconductor layer 31.

The first photodiode PD1 is provided so as to overlap with the second photodiode PD2. To be specific, the first partial semiconductor layer 31a of the first photodiode PD1 overlaps with the second photodiode PD2. The second photodiode PD2 includes a second semiconductor layer 51, the cathode electrode 54, and the anode electrode 55. The second semiconductor layer 51 is made of, for example, polysilicon. More preferably, the second semiconductor layer 51 is made of low-temperature polycrystalline silicone (hereinafter, referred to as LTPS).

The second semiconductor layer 51 has an i region 52a, a p region 52b, and an n region 52c. The i region 52a is arranged between the p region 52b and the n region 52c when seen from above. To be specific, the p region 52b, the i region 52a, and the n region 52c are arranged in this order in the first direction Dx. In the n region 52c, polysilicon is doped with impurities to form an n+ region. In the p region 52b, polysilicon is doped with impurities to form a p+ region. The i region 52a is, for example, a non-doped intrinsic semiconductor and has lower conductivity than those of the p region 52b and the n region 52c.

The second semiconductor layer 51 and the first partial semiconductor layer 31a of the first photodiode PD1 are coupled to each other through a first relay electrode 56 and a second relay electrode 57. In the embodiment, a portion of the first relay electrode 56 that overlaps with the second semiconductor layer 51 functions as the cathode electrode 54. A portion of the second relay electrode 57 that overlaps with the second semiconductor layer 51 functions as the anode electrode 55. The detail coupling configuration between the second semiconductor layer 51 and the first photodiode PD1 will be described later.

The first switching element Tr is provided in a region overlapping with the second partial semiconductor layer 31b of the first photodiode PD1. The first switching element Tr includes a third semiconductor layer 61, a source electrode 62, a drain electrode 63, and gate electrodes 64. The third semiconductor layer 61 is made of polysilicon similarly to the second semiconductor layer 51. The third semiconductor layer 61 is made of LTPS more preferably.

In the embodiment, a portion of the first relay electrode 56 that overlaps with the third semiconductor layer 61 functions as the source electrode 62. A portion of the signal line SGL that overlaps with the third semiconductor layer 61 functions as the drain electrode 63. The gate electrodes 64 branches from the gate line GCL in the second direction Dy and overlap with the third semiconductor layer 61. In the embodiment, two gate electrodes 64 have what is called a double gate structure in which they are provided so as to overlap with the third semiconductor layer 61.

The first switching element Tr is coupled to the cathode electrode 34 of the first photodiode PD1 and the cathode electrode 54 of the second photodiode PD2 through the first relay electrode 56. The first switching element Tr is coupled to the signal line SGL as well.

To be more specific, as illustrated in FIG. 9, the first switching element Tr is provided on the insulating substrate 21. The insulating substrate 21 is a glass substrate having a light-transmitting property, for example. Alternatively, the insulating substrate 21 may be a resin substrate or a resin film made of resin such as polyimide having a light-transmitting property. The first sensor 10A has the configuration in which the first photodiode PD1, the second photodiode PD2, and the first switching element Tr are formed above the insulating substrate 21.

Light shielding layers 67 and 68 are above the insulating substrate 21. An undercoat film 22 covers the light shielding layers 67 and 68 and is provided above the insulating substrate 21. The undercoat film 22, a gate insulating film 23, and a first interlayer insulating film 24 are inorganic insulating films and are formed by a silicon oxide film (SiO), a silicon nitride film (SiN), a silicon oxide nitride film (SiON), or the like. Each inorganic insulating film is not limited to a single layer and may be a multilayered film.

The second semiconductor layer 51 and the third semiconductor layer 61 are provided above the undercoat film 22. That is to say, the second semiconductor layer 51 of the second photodiode PD2 and the third semiconductor layer 61 of the first switching element Tr are provided in the same layer. The light shielding layer 67 is provided between the second semiconductor layer 51 and the insulating substrate 21 in the third direction Dz. Light L1 from the light source unit 110 (see FIG. 3) can thereby be prevented from being emitted directly to the second photodiode PD2. The light shielding layer 68 is provided between the third semiconductor layer 61 and the insulating substrate 21 in the third direction Dz. This can prevent light leak current of the first switching element Tr.

The third semiconductor layer 61 has i regions 61a, lightly doped drain (LDD) regions 61b, and n regions 61c. The i regions 61a are formed in regions overlapping with the gate electrodes 64. The n regions 61c are high-concentration impurity regions and are formed in regions coupled to the source electrode 62 and the drain electrode 63. The LDD regions 61b are low-concentration impurity regions and are formed between the n regions 61c and the i regions 61a and between the two i regions 61a.

The gate insulating film 23 covers the second semiconductor layer 51 and the third semiconductor layer 61 and is provided above the undercoat film 22. The gate electrodes 64 are provided above the gate insulating film 23. That is to say, the first switching element Tr has what is called a top gate structure in which the gate electrodes 64 are provided on the upper side of the third semiconductor layer 61. The first switching element Tr may have what is called a dual gate structure in which the gate electrodes 64 are provided on both of the upper side and the lower side of the third semiconductor layer 61 or a bottom gate structure in which the gate electrodes 64 are provided on the lower side of the third semiconductor layer 61.

The first interlayer insulating film 24 covers the gate electrodes 64 and is provided above the gate insulating film 23. The first interlayer insulating film 24 is provided also on the upper side of the second semiconductor layer 51. The first relay electrode 56, the second relay electrode 57, and the signal lines SGL are provided above the first interlayer insulating film 24. The source electrode 62 (first relay electrode 56) is coupled to the third semiconductor layer 61 through a contact holes H8 in the first switching element Tr. The drain electrode 63 (signal line SGL) is coupled to the third semiconductor layer 61 through a contact hole H7.

In the second photodiode PD2, the cathode electrode 54 (first relay electrode 56) is coupled to the n region 52c of the second semiconductor layer 51 through a contact hole H6.

The cathode electrode 54 of the second photodiode PD2 is coupled to the first switching element Tr. The anode electrode 55 (second relay electrode 57) is coupled to the p region 52b of the second semiconductor layer 51 through a contact holes H5.

A second interlayer insulating film 25 covers the second photodiode PD2 and the first switching element Tr and is provided above the first interlayer insulating film 24. The second interlayer insulating film 25 is an organic film and is a flattening film flattening irregularities formed by various conductive layers. The second interlayer insulating film 25 may be made of the above-mentioned inorganic material.

The anode electrode 35 of the first photodiode PD1 is provided above the second interlayer insulating film 25 of a backplane 19. The first photodiode PD1 is configured by stacking the anode electrode 35, the first partial semiconductor layer 31a and the second partial semiconductor layer 31b, and the cathode electrode 34 in this order. The backplane 19 is a drive circuit board driving the sensor for each predetermined detection region. The backplane 19 includes the insulating substrate 21, and the first switching elements Tr, the second switching elements TrG, and various wiring provided on the insulating substrate 21, and the like.

The first partial semiconductor layer 31a includes an i-type semiconductor layer 32a, a p-type semiconductor layer 32b, and an n-type semiconductor layer 32c. The second partial semiconductor layer 31b includes an i-type semiconductor layer 33a, a p-type semiconductor layer 33b, and an n-type semiconductor layer 33c. The i-type semiconductor layers 32a and 33a, the p-type semiconductor layers 32b and 33b, and the n-type semiconductor layers 32c and 33c are specific examples of photoelectric conversion elements. In FIG. 9, the i-type semiconductor layers 32a and 33a are provided between the p-type semiconductor layers 32b and 33b and the n-type semiconductor layers 32c and 33c in the direction perpendicular to the surface of the insulating substrate 21 (third direction Dz). In the embodiment, the p-type semiconductor layers 32b and 33b, the i-type semiconductor layers 32a and 33a, and the n-type semiconductor layers 32c and 33c are stacked in this order above the anode electrode 35.

In the n-type semiconductor layers 32c and 33c, a-Si is doped with impurities to form n+ regions. In the p-type semiconductor layers 32b and 33b, a-Si is doped with impurities to form p+ regions. The i-type semiconductor layers 32a and 33a are, for example, non-doped intrinsic semiconductors and have lower conductivity than those of the n-type semiconductor layers 32c and 33c and the p-type semiconductor layers 32b and 33b.

The cathode electrode 34 and the anode electrode 35 are made of a conductive material having a light transmitting property, such as indium tin oxide (ITO). The cathode electrode 34 is an electrode for supplying the power supply signal SVS to the photoelectric conversion layer. The anode electrode 35 is an electrode for reading the detection signal Vdet.

The anode electrode 35 is provided above the second interlayer insulating film 25. The anode electrode 35 is provided continuously for the first partial semiconductor layer 31a and the second partial semiconductor layer 31b. The anode electrode 35 is coupled to the second relay electrode 57 through a contact hole H4 provided in the second interlayer insulating film 25.

A third interlayer insulating film 26 is provided so as to cover the first partial semiconductor layer 31a and the second partial semiconductor layer 31b. The third interlayer insulating film 26 is an organic film and is a flattening film flattening irregularities formed by the first partial semiconductor layer 31a and the second partial semiconductor layer 31b. The cathode electrode 34 is provided above the third interlayer insulating film 26. The cathode electrode 34 is provided continuously above the first partial semiconductor layer 31a and the second partial semiconductor layer 31b. The cathode electrode 34 is coupled to the first partial semiconductor layer 31a and the second partial semiconductor layer 31b through contact holes H2 and H1 provided in the third interlayer insulating film 26. The first partial semiconductor layer 31a and the second partial semiconductor layer 31b are thereby coupled in parallel between the anode electrode 35 and the cathode electrode 34 and function as one photoelectric conversion element.

The cathode electrode 34 is coupled to the first relay electrode 56 through a contact hole H3 in the space SP between the first partial semiconductor layer 31a and the second partial semiconductor layer 31b. The contact hole H3 is a through-hole penetrating through the second interlayer insulating film 25 and the third interlayer insulating film 26 in the third direction Dz. An opening 35a is provided in a part of the anode electrode 35 that overlaps with the contact hole H3, and the contact hole H3 is formed through the opening 35a. With this configuration, the cathode electrode 34 of the first photodiode PD1 and the cathode electrode 54 of the second photodiode PD2 are coupled to the first switching element Tr through the first relay electrode 56. The anode electrode 35 of the first photodiode PD1 and the anode electrode 55 of the second photodiode PD2 are coupled to each other through the second relay electrode 57.

The capacitance of the capacitor element Ca illustrated in FIG. 6 is formed between the anode electrode 55 and the cathode electrode 34 facing each other with the third interlayer insulating film 26 interposed therebetween in the space SP. Alternatively, the capacitance of the capacitor element Ca is formed between the anode electrode 55 and the cathode electrode 34 facing each other with the third interlayer insulating film 26 interposed therebetween in a space Spa at the peripheral edge of the first photodiode PD1. Positive electric charges are held in the capacitor element Ca in the exposure period Pex.

The first sensor 10A has the above-mentioned configuration. That is to say, the first sensor 10A includes the first photodiode PD1 having the first semiconductor layers 31 containing amorphous silicon and the second photodiode PD2 having the second semiconductor layer 51 containing polysilicon. The first sensor 10A has the configuration in which the first semiconductor layers 31 containing amorphous silicon and the second semiconductor layer 51 containing polysilicon, that is, the first photodiode PD1 and the second photodiode PD2 are stacked so as to overlap with each other in the third direction Dz. In the first sensor 10A, the first photodiode PD1 and the second photodiode PD2 may not be stacked in the third direction Dz and may be provided in the same layer.

Figure 10:
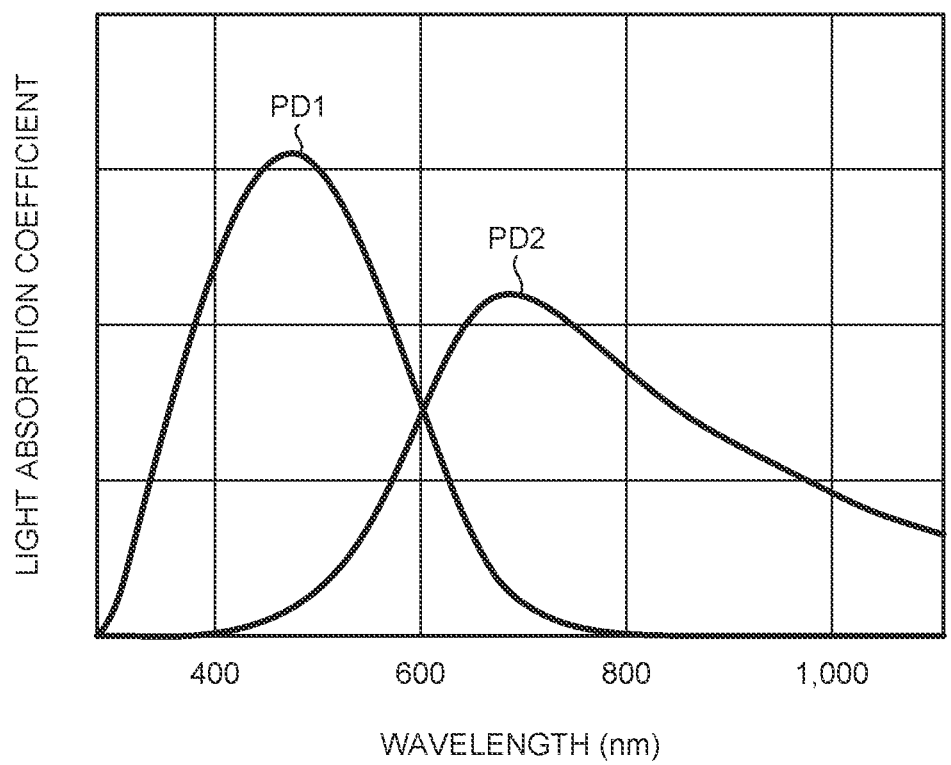
FIG. 10 is a graph schematically illustrating a relation between a wavelength and a light absorption coefficient for a first photodiode and a second photodiode.

Next, light absorption of the first photodiode PD1 and the second photodiode PD2 will be described. FIG. 10 is a graph schematically illustrating a relation between a wavelength and a light absorption coefficient for the first photodiode and the second photodiode. A transverse axis in FIG. 10 indicates the wavelength and a longitudinal axis indicates the light absorption coefficient. The light absorption coefficient is an optical constant indicating the degree of absorption of light traveling in a substance.

As illustrated in FIG. 10, the first photodiode PD1 containing amorphous silicon exhibits a preferable light absorption coefficient in a visible light region, for example, a wavelength region of 300 nm to 800 nm. On the other hand, the second photodiode PD2 containing polysilicon exhibits a preferable light absorption coefficient in a region including the visible light region to an infrared region, for example, a wavelength region of 500 nm to 1100 nm. In other words, the first photodiode PD1 has high sensitivity in the visible light region, and the second photodiode PD2 has high sensitivity in a red wavelength region to the infrared region as a wavelength region differing from that of the first photodiode PD1.

In the first sensor 10A in the embodiment, the first photodiodes PD1 and the second photodiodes PD2 having different sensitive wavelength regions are stacked. The wavelength region having sensitivity can therefore be enlarged in comparison with the configuration in which any one of the photodiodes is provided.

The light L1 (see FIG. 3) passes through the detection device 100 through the space SP and the space SPa. The light L2 (see FIG. 3) reflected by the finger Fg is incident on the first photodiode PD1. Light of a wavelength region that is not absorbed by the first photodiode PD1 in the light L2 passes through the first photodiode PD1 and is incident on the second photodiode PD2. For example, the first photodiode PD1 can preferably detect the light L2 in blue or green in the fingerprint detection. The light L2 of infrared light is not absorbed by the first photodiode PD1 and is incident on the second photodiode PD2 in the defect pattern detection. The second photodiode PD2 can thereby preferably detect the light L2 of infrared light. Accordingly, the first sensor 10A can detect various pieces of information related to a living body.

Even when the i region 52a of the second photodiode PD2 is made into an n type due to influences by charging of the insulating film such as the first interlayer insulating film 24 or impurities, the i region 52a is neutralized by the cathode electrode 34 of the first photodiode PD1. The detection device 100 can therefore improve light sensitivity.

The first photodiode PD1 and the second photodiode PD2 are provided in the partial detection region PAA, that is, the region surrounded by the gate lines GCL and the signal lines SGL. With this configuration, the number of switching elements and the number of wiring lines can be reduced in comparison with the case in which the first switching element Tr, the gate line GCL, and the signal line SGL are provided for each of the first photodiode PD1 and the second photo diode PD2. The detection device 100 can therefore improve the resolution of detection.

Figure 11:
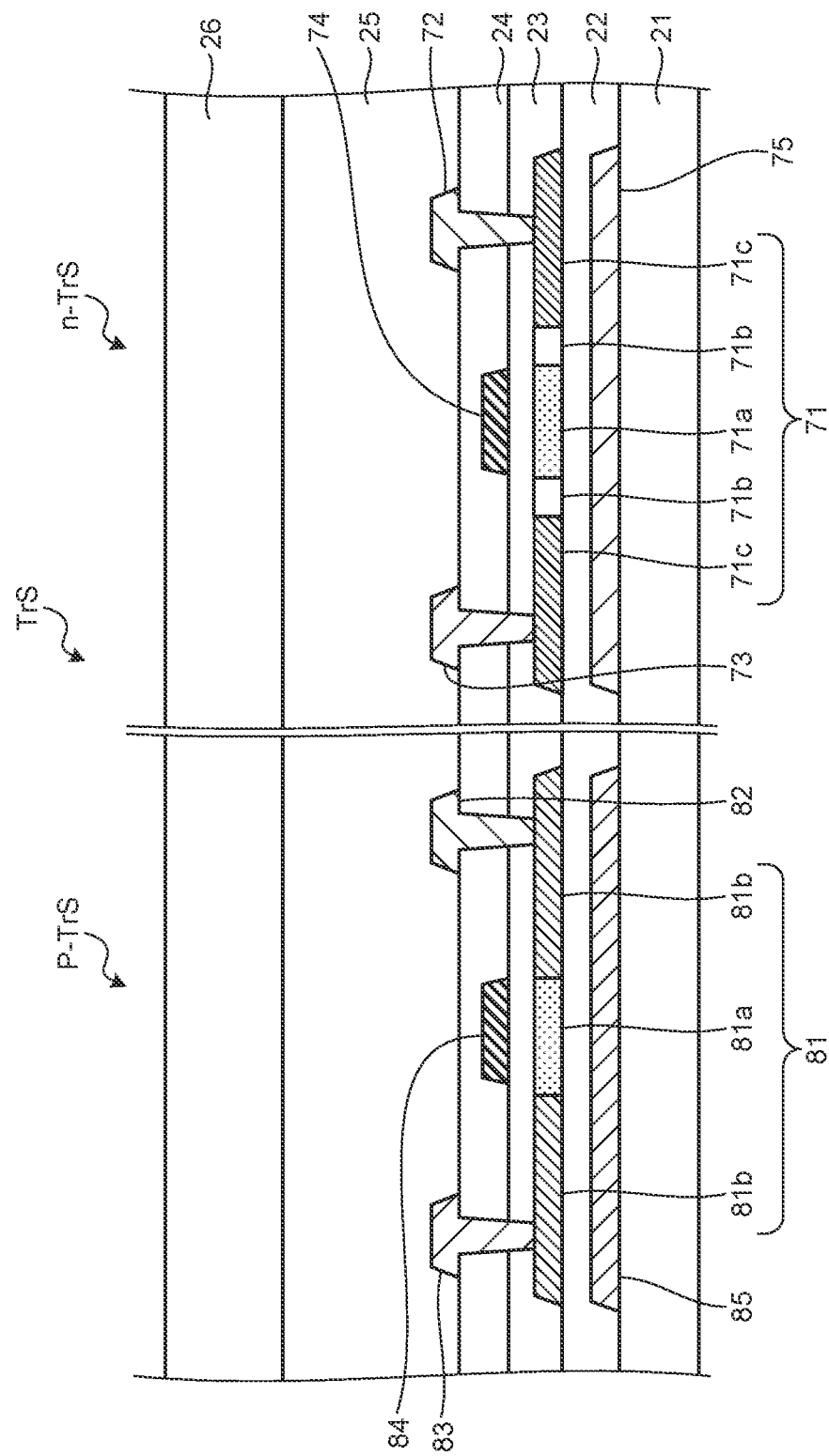
FIG. 11 is a cross-sectional view illustrating the schematic cross-sectional configuration of a switching element that a drive circuit includes.

Subsequently, the third switching element TrS and the fourth switching element TrR will be described. FIG. 11 is a cross-sectional view illustrating the schematic cross-sectional configuration of the switching element that the drive circuit includes. FIG. 11 illustrates the third switching element TrS that the signal line selection circuit 16 includes as a drive circuit switching element. Explanation of FIG. 11 can also be applied to the switching elements that other drive circuits include. In other words, the configuration similar to that in FIG. 11 can be applied to the second switching elements TrG that the gate line drive circuit 15 includes and the fourth switching elements TrR that the reset circuit 17 includes.

As illustrated in FIG. 11, the n-channel transistor n-TrS of the third switching element TrS includes a fourth semiconductor layer 71, a source electrode 72, a drain electrode 73, and a gate electrode 74. The p-channel transistor p-TrS includes a fifth semiconductor layer 81, a source electrode 82, a drain electrode 83, and a gate electrode 84. A light shielding layer 75 is provided between the fourth semiconductor layer 71 and the insulating substrate 21, and a light shielding layer 85 is provided between the fifth semiconductor layer 81 and the insulating substrate 21.

Both of the fourth semiconductor layer 71 and the fifth semiconductor layer 81 are made of polysilicon. The fourth semiconductor layer 71 and the fifth semiconductor layer 81 are made of LTPS more preferably. The fourth semiconductor layer 71 has an i region 71a, LDD regions 71b, and n regions 61c. The fifth semiconductor layer 81 has an i region 81a and p regions 81b.

The layer structures of the n-channel transistor n-TrS and the p-channel transistor p-TrS are similar to that of the first switching element Tr illustrated in FIG. 9. That is to say, the fourth semiconductor layer 71 and the fifth semiconductor layer 81 are provided in the same layer as the second semiconductor layer 51 and the third semiconductor layer 61 illustrated in FIG. 9. The gate electrode 74 and the gate electrode 84 are provided in the same layer as the gate electrodes 64 illustrated in FIG. 9. The source electrode 72, the drain electrode 73, the source electrode 82, and the drain electrode 83 are provided in the same layer as the source electrode 62 (first relay electrode 56) and the drain electrode 63 (signal lines SGL) illustrated in FIG. 9.

As described above, the first photodiode PD1 and the first switching element Tr, and the switching element such as the third switching element TrS are made of the same material and provided in the same layer in the first sensor 10A. A manufacturing process of the detection device 100 is thereby simplified, thereby reducing manufacturing cost. The third switching elements TrS are not limited to be configured by the CMOS transistors and may be configured by either of the n-channel transistors n-TrS or the p-channel transistors p-TrS. The materials and the multilayered configuration of the first sensor 10A are not limited to the above-mentioned ones.

Configuration of Second Sensor

Figure 12:
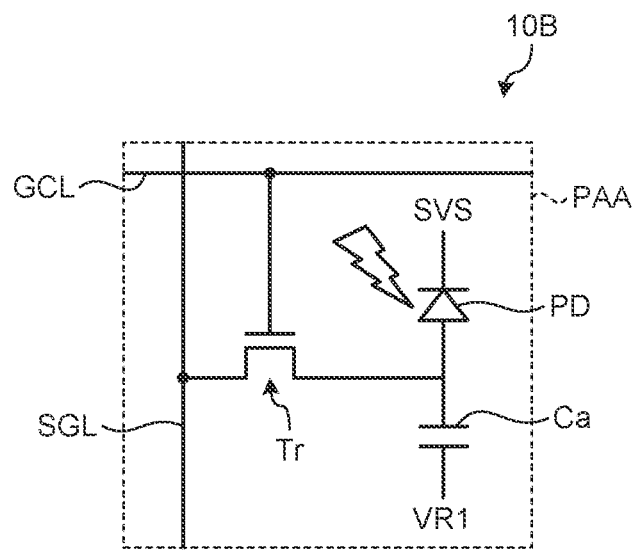
FIG. 12 is an equivalent circuit diagram illustrating a second sensor according to the first embodiment.

Next, the configuration of the second sensor 10B will be described. The circuit configuration including the second sensor 10B is similar to the circuit configuration illustrated in FIG. 5, and description thereof is omitted. FIG. 12 is an equivalent circuit diagram illustrating the second sensor in the first embodiment. As illustrated in FIG. 12, the second sensor 10B has the partial detection regions PAA arrayed in a matrix with a row-column configuration. As illustrated in FIG. 12, the partial detection region PAA of the second sensor 10B includes the second photodiode PD2, the capacitor element Ca, and the first switching element Tr. The first switching element Tr is provided so as to correspond to the second photodiode PD2. The gate of the first switching element Tr is coupled to the gate line GCL. The source of the first switching element Tr is coupled to the signal line SGL. The drain of the first switching element Tr is coupled to the cathode electrode 54 of the second photodiode PD2 and one terminal of the capacitor element Ca. The anode electrode 55 of the second photodiode PD2 and the other terminal of the capacitor element Ca are coupled to a reference potential, for example, a ground potential. That is to say, the second sensor 10B does not include the first photodiode PD1 unlike the first sensor 10A. The second sensor 10B may be configured to be capable of detecting the fingerprint, palm print, or the like of the user. In this case, the second sensor 10B may have a similar configuration to that of the first sensor 10A, for example.

Figure 13:
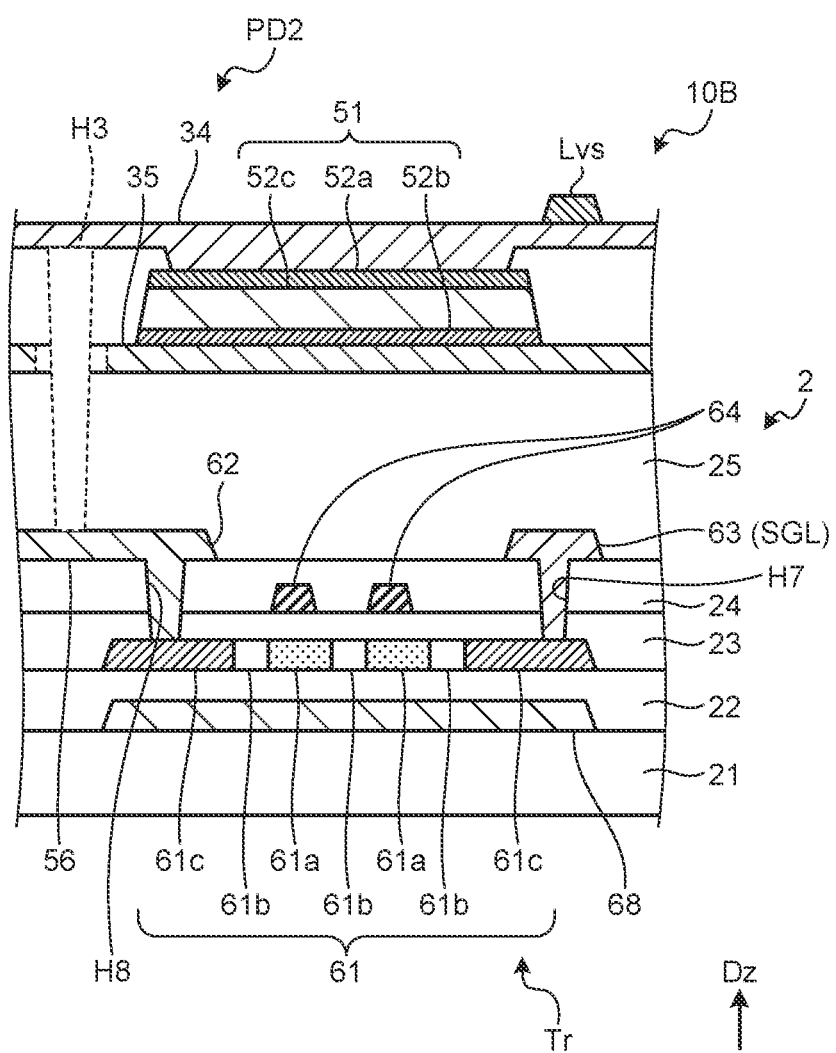
FIG. 13 is a schematic cross-sectional view of a partial detection region of the second sensor.

FIG. 13 is a schematic cross-sectional view of the partial detection region of the second sensor. As illustrated in FIG. 13, the second sensor 10B includes the first switching element Tr above the insulating substrate 21 similarly to the first sensor 10A illustrated in FIG. 9 does. The second sensor 10B includes no first photodiode PD1 unlike the first sensor 10A. The second sensor 10B is different from the first sensor 10A in position at which the second photodiode PD2 is provided. The second photodiode PD2 is provided on the upper side, that is, the third direction Dz side of the first switching element Tr in the second sensor 10B. That is to say, the anode electrode 35 of the second photodiode PD2 is provided above the second interlayer insulating film 25. The second photodiode PD2 is configured by stacking the anode electrode 35, the second semiconductor layer 51, and the cathode electrode 34 in this order. The second semiconductor layer 51 is configured by stacking the p region 52b, the i region 52a, and the n region 52c in this order above the anode electrode 35. The anode electrode 35 is coupled to the source electrode 62 of the first switching element Tr through the contact hole H4 provided in the second interlayer insulating film 25. The multilayered configurations of the third switching elements TrS and the fourth switching elements TrR in the second sensor 10B are similar to those in FIG. 11.

The second sensor 10B includes the second photodiode PD2 having the second semiconductor layer 51 containing polysilicon as described above and can therefore detect the blood vessel pattern of the user preferably. The materials and the multilayered configuration of the second sensor 10B are not limited to the above-mentioned ones.

When the first sensor 10A detects the fingerprint of the user and does not detect the blood vessel pattern of the user, the first sensor 10A may not include the second photodiode PD2 and include the first photodiode PD1. In this case, the equivalent circuit of the first sensor 10A is provided by replacing the second photodiode PD2 in FIG. 12 by the first photodiode PD1, and the multilayered configuration of the first sensor 10A is preferably configured by replacing the second photodiode PD2 by the first photodiode PD1 in FIG. 13.

Authentication Flow

Figure 14A:
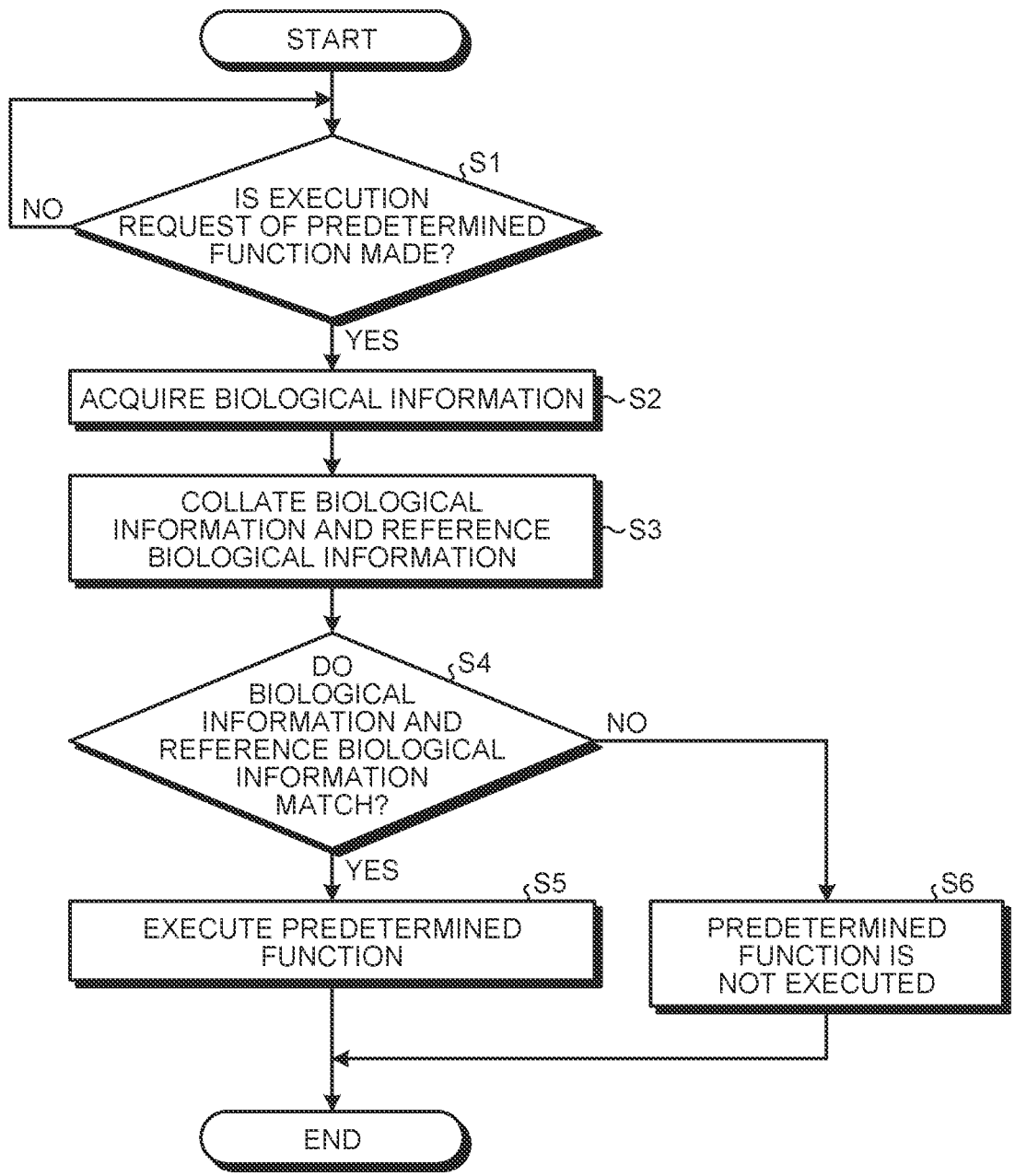
FIG. 14A is a flowchart for explaining flow of user authentication.

Next, flow of user authentication using the sensor 10 configured as described above will be described. FIG. 14A is a flowchart for explaining the flow of the user authentication. As illustrated in FIG. 14A, the detection device 100 determines by the controller 6 whether an execution request of a predetermined function is made (step S1). The user operates the input unit 1 in which the sensor 10 is provided to request execution of the predetermined function (activation of the detection device 100, restoration from a sleep state, activation of a computer program, access to a web site, or the like) from the detection device 100. In other words, a function of receiving the execution request of the predetermined function from the user can be assigned to the input unit 1 in which the sensor 10 is provided. The controller 6 acquires, from the input unit 1, information indicating that the input unit 1 has been operated and determines whether the function of receiving the execution request of the predetermined function is assigned to the input unit 1. The controller 6 determines that the execution request of the predetermined function is made when the function of receiving the execution request of the predetermined function is assigned to the operated input unit 1. On the other hand, the controller 6 determines that the execution request of the predetermined function is not made when the function of receiving the execution request of the predetermined function is not assigned to the operated input unit 1.

When the execution request of the predetermined function is made (Yes at step S1), the controller 6 acquires the biological information of the user (step S2). More specifically, the controller 6 acquires, from the sensor 10, the biological information of the user in the operation of requesting the execution of the predetermined function. The sensor 10 detects the biological information of the user when there is proximity to the input unit 1 configured to receive the execution request of the predetermined function, that is, the user operates the input unit 1. To be specific, the sensor 10 outputs, to the detector 40 (see FIG. 4), the detection signals Vdet corresponding to the light L2 reflected by the finger Fg or the palm of the hand of the user that is proximate to the input unit 1 through the signal line selection circuit 16 (see FIG. 4). The detector 40 generates the biological information (in this example, the two-dimensional information of the fingerprint or the blood vessel pattern) of the user based on the detection signals Vdet by the coordinate extraction unit 45 and outputs the biological information to the controller 6. As described above, when the execution request of the predetermined function is received and the operation of requesting the execution of the predetermined function is made to the input unit 1 in which the sensor 10 is provided, the controller 6 acquires, from the sensor 10, the biological information of the user in the operation of requesting the execution. When the execution request of the predetermined function is not made (No at step S1), the process returns to step S1 and continues receiving the execution request of the predetermined function. The sensor 10 may start driving with the execution request of the predetermined function as a trigger or may be driven all the time.

When the biological information of the user is acquired, the controller 6 collates the biological information of the user and the reference biological information (step S3) and determines whether the biological information of the user and the reference biological information match (step S4). To be specific, the controller 6 reads, from the storage unit 8, the reference biological information being the previously stored reference biological information. The reference biological information is previously stored as the biological information (in this example, the two-dimensional information of the fingerprint or the blood vessel pattern) of the user that is permitted to use the predetermined function, for example. The controller 6 collates the biological information of the user and the reference biological information and determines whether the biological information of the user matches the reference biological information. For example, the controller 6 may pattern-collate the biological information of the user and the reference biological information to determine that the biological information of the user matches the reference biological information when the similarity of feature points is equal to or higher than a predetermined degree, and determine that the biological information of the user does not match the reference biological information when the similarity of the feature points is less than the predetermined degree, for example. The biological information of the user and the reference biological information may be collated with each other by a well-known technique.

When the controller 6 determines that the biological information of the user and the reference biological information match (Yes at step S4), the controller 6 determines that the authentication is affirmative and controls the detection device 100 to execute the predetermined function for which the execution request has been made (step S5). When the controller 6 determines that the biological information of the user and the reference biological information do not match (No at step S4), the controller 6 determines that the authentication is negative and does not execute the predetermined function (step S6). This process is finished with step S5 or step S6 described above. Even when it is determined that the authentication is negative and the process proceeds to step S6, the process may return to step S2 and the authentication processing may be continued if proximity to the user is detected. Even after it is determined that the authentication is affirmative and step S5 is executed, the process may return to step S2 and the authentication processing may be continued every predetermined time.

As described above, the detection device 100 in the embodiment performs the authentication based on the biological information in the operation of requesting the execution of the predetermined function by the user. Then, it executes the predetermined function when the authentication is affirmative. That is to say, the detection device 100 performs the authentication operation and the execution operation of the predetermined function based on only the operation of requesting the execution of the predetermined function. Accordingly, the detection device 100 eliminates the necessity of an operation only for the authentication and enables the authentication and the execution of the predetermined function only by performing the operation of requesting the execution of the predetermined function (for example, an application activation operation), thereby enabling reduction of the labor and time for the authentication.

Figure 14B:
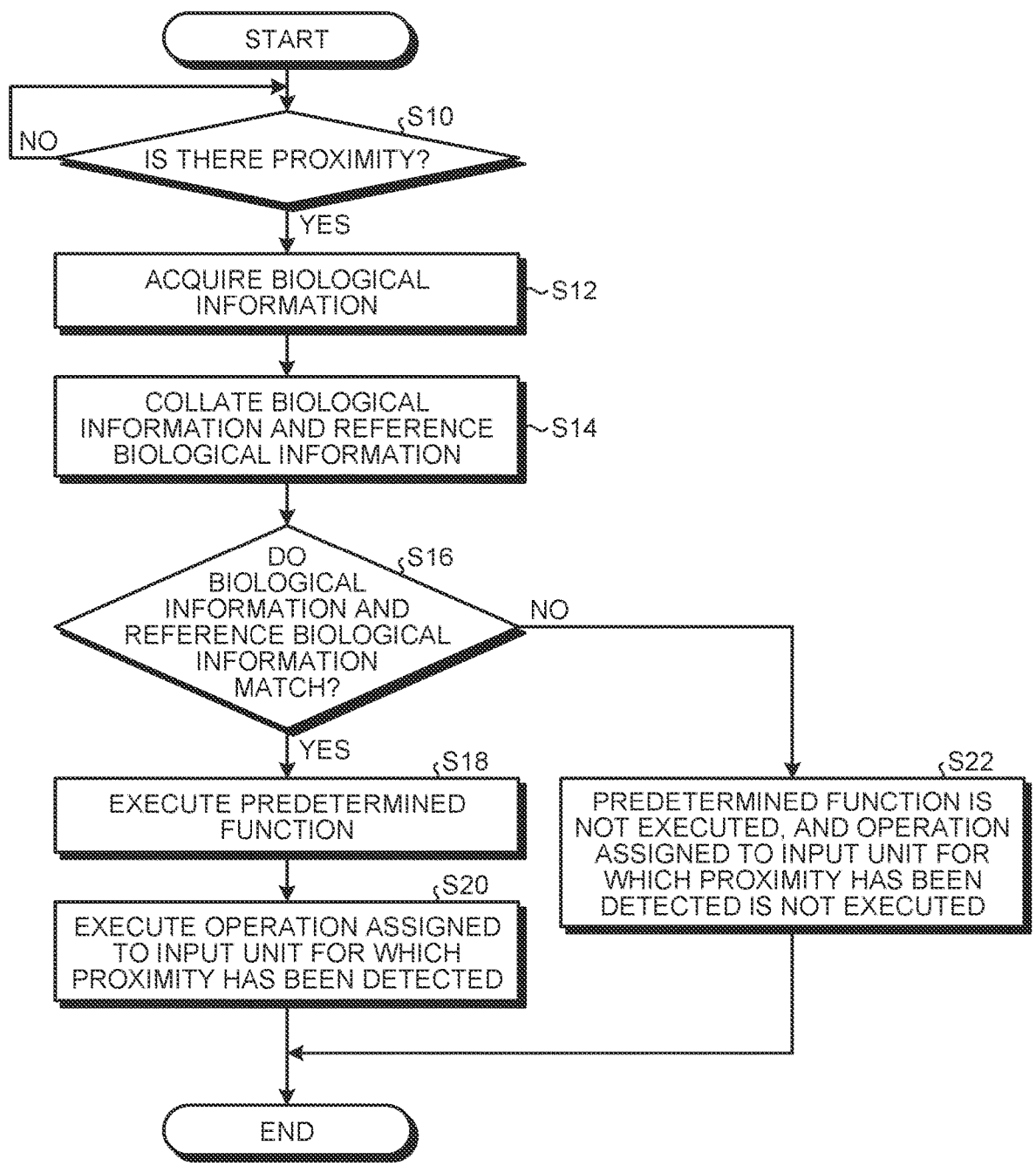
FIG. 14B is a flowchart for explaining flow of user authentication.

As illustrated in FIG. 14B below, when the user operates the input unit 1, the detection device 100 may execute an operation assigned to the input unit 1 in addition to the authentication processing and the execution of the predetermined function. FIG. 14B is a flowchart for explaining flow of the user authentication.

As illustrated in FIG. 14B, the detection device 100 detects whether there is proximity to the input unit 1 in which the sensor 10 is provided (step S10). That is to say, the detection device 100 detects whether the finger Fg or the palm of the hand of the user is proximate to the input unit 1 in which the sensor 10 is provided. For example, the detection device 100 detects light L2 (see FIG. 3) reflected by the input unit 1 while driving the sensor 10 all the time to detect, by the sensor 10, whether the finger Fg or the palm of the hand of the user is proximate to the input unit 1. For example, in the detection device 100, the controller 6 (see FIG. 4) may acquire information of the light L2 that the sensor 10 has detected and determine whether the finger Fg or the palm of the hand of the user is proximate to the input unit 1 based on the information of the light L2. In this case, when the intensity of the light L2, in this example, the detection signal Vdet output from the sensor 10 is equal to or higher than a predetermined threshold, the controller 6 determines that the finger Fg or the palm of the hand of the user is proximate to the input unit 1. When the intensity of the light L2 is lower than the threshold, the controller 6 determines that the finger Fg or the palm of the hand of the user is not proximate to the input unit 1. The user performs character input, for example, to the detection device 100 by pressing a key of the input unit 1 in which the sensor 10 is provided. The controller 6 may recognize the proximity of the user when the user presses the key.

When it is determined that there is proximity to the input unit 1 in which the sensor 10 is provided (Yes at step S10), the detection device 100 acquires the biological information of the user (step S12). That is to say, the sensor 10 provided in the input unit 1 for which the proximity has been detected detects the biological information of the user when the user operates the input unit 1. The controller 6 acquires, from the sensor 10, the biological information of the user when the user operates the input unit 1. When it is determined that there is no proximity to the input unit 1 in which the sensor 10 is provided, at step S10 (No at step S10), the process returns to step S10 and detection of the proximity is continued.

When the biological information of the user is acquired, in the detection device 100, the controller 6 collates the biological information of the user and the reference biological information (step S14) and determines whether the biological information of the user and the reference biological information match (step S16). When the controller 6 determines that the biological information of the user and the reference biological information match (Yes at step S16), the controller 6 controls the detection device 100 to execute the predetermined function that has been previously defined (step S18). The predetermined function may be a function that has been previously set. That is to say, the predetermined function may be previously set to the detection device 100 as a function to be executed when the user operates the input unit 1. The predetermined function may, however, be a function that the user has requested to execute by the operation.

When the controller 6 determines that the biological information of the user and the reference biological information match, in other words, determines that the predetermined function is executed, it executes the operation assigned to the input unit 1 for which the proximity has been detected, in addition to execution of the predetermined function (step S20). In other words, the operation assigned to the input unit 1 for which the proximity has been detected is an operation assigned to the input unit 1 operated by the user when the sensor 10 has detected the biological information in the predetermined function (for example, the activated computer program) executed at step S18. When the predetermined function is activation of the computer program and an enter key as the input unit 1 is operated, for example, the detection device 100 executes processing corresponding to input to the enter key as the operation assigned to the enter key for which the proximity has been detected, in the activated computer program. As described above, when the user operates the input unit 1 in which the sensor 10 is provided, the detection device 100 detects the proximity of the user to the input unit 1, detects the biological information of the user by the sensor 10 provided in the input unit 1, and collates the biological information of the user and the reference biological information by the controller 6. When the biological information of the user and the reference biological information match by collation, the detection device 100 receives input to the input unit 1 and executes the operation assigned to the input unit 1, in addition to the execution of the predetermined function.

When the controller 6 determines that the biological information of the user and the reference biological information do not match (No at step S16), the controller 6 does not execute the predetermined function and does not execute the operation assigned to the input unit 1 for which the proximity has been detected (step S22). That is to say, when the controller 6 determines that the predetermined function is not executed, it does not execute the operation assigned to the input unit 1 for which the proximity has been detected.

As described above, the detection device 100 according to the first embodiment includes the input unit 1 configured to receive the operation of the user and the sensor 10 provided in the input unit 1 and configured to detect the biological information of the user when the user operates the input unit 1. In the detection device 100, the sensor 10 detects the biological information of the user when the user operates the input unit 1. Accordingly, the detection device 100 enables the authentication with the biological information only by the operation for operating the detection device 100 (for example, the operation of requesting the execution of the predetermined function) by the user. The detection device 100 can therefore eliminate the necessity of the operation only for the authentication, such as input of a password by the user and a user operation on a fingerprint authentication screen, thereby reducing the labor and time for the authentication.

The detection device 100 includes the controller 6 configured to determine whether the predetermined function is executed based on the biological information of the user that the sensor 10 has detected. When the user inputs the operation of requesting the execution of the predetermined function to the input unit 1, the controller 6 acquires, from the sensor 10, the biological information of the user in the operation of requesting the execution of the predetermined function and determines whether the predetermined function is executed based on the acquired biological information of the user. The detection device 100 includes the controller 6, thereby enabling the authentication to be performed appropriately. More specifically, the detection device 100 eliminates the necessity of the user operation only for the authentication and enables the authentication and the execution of the predetermined function only by performing the operation of requesting the execution of the predetermined function, thereby enabling reduction of the labor and time for the authentication. The detection device 100 may not include the controller 6. In this case, for example, the detection device 100 may transmit, to another device (external server or the like) including the controller 6, the biological information of the user that the sensor 10 has detected, and the other device may perform the authentication by the controller 6 and transmit an authentication result to the detection device 100.

When the controller 6 determines that the predetermined function is not executed, that is, determines that the biological information of the user and the reference biological information do not match, it does not execute the operation assigned to the input unit 1 operated by the user in the detection of the biological information. When the controller 6 determines that the predetermined function is executed, it executes the operation assigned to the input unit 1 operated by the user in the detection of the biological information. The detection device 100 executes the predetermined function and executes the operation assigned to the input unit 1 in the predetermined function when the authentication is affirmative. That is to say, the detection device 100 not only performs the authentication and executes the predetermined function but also performs the operation in the predetermined function by the operation to the input unit 1 by the user. The necessity of the operation only for the authentication is therefore eliminated, thereby enabling reduction of the labor and time for the authentication.

In the first embodiment, the sensor 10 includes the first sensor 10A configured to detect the fingerprints of the user and the second sensor 10B configured to detect the blood vessel patterns of the user. Such inclusion of the first sensor 10A and second sensor 10B enables the authentication based on a plurality of types of biological information, thereby enabling accuracy of the authentication to be enhanced. For example, the detection device 100 may determine that the authentication is affirmative and execute the predetermined function when the biological information (fingerprint) of the user that the first sensor 10A has acquired matches the reference biological information (fingerprint in the reference biological information) and the biological information (blood vessel pattern) of the user that the second sensor 10B has acquired matches the reference biological information (blood vessel pattern in the reference biological information). The detection device 100 may acquire any one of the biological information of the user that the first sensor 10A has acquired and the biological information of the user that the second sensor 10B has acquired, and determine that the authentication is affirmative and execute the predetermined function when the acquired one biological information matches the reference biological information. The detection device 100 may thereafter acquire the other of the biological information of the user that the first sensor 10A has acquired and the biological information of the user that the second sensor 10B has acquired, and interrupt the execution of the predetermined function when the other acquired biological information does not match the reference biological information.

The first sensor 10A includes the semiconductor (first semiconductor layer 31) containing amorphous silicon, and the second sensor 10B includes the semiconductor (second semiconductor layer 51) containing polysilicon. Accordingly, the detection device 100 can preferably detect the fingerprint and the blood vessel pattern of the user.

Figure 15:
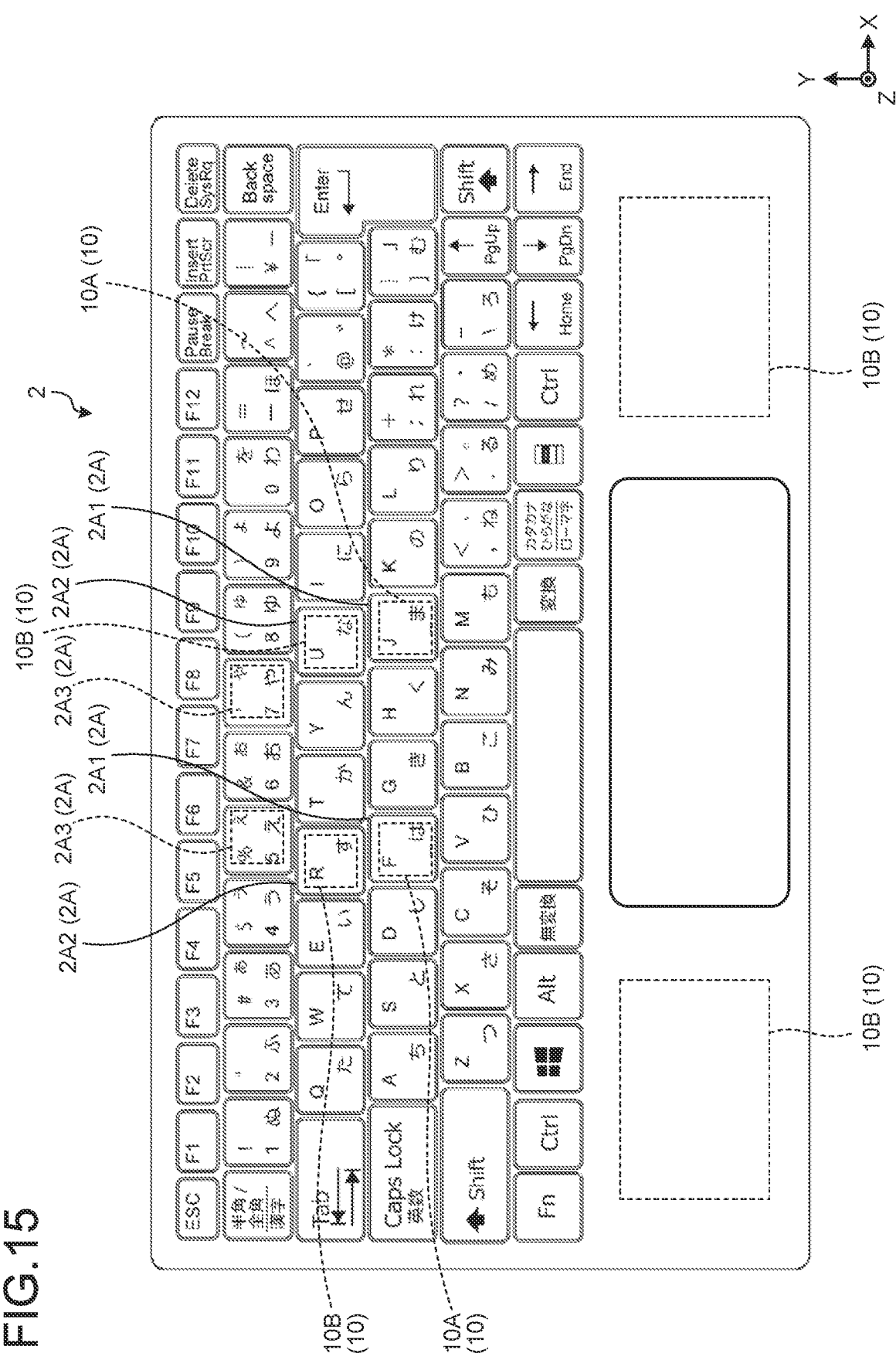
FIG. 15 is a view illustrating another example of the keyboard.

In the example of FIG. 2, the first sensors 10A are provided in the buttons 2A of the keyboard 2, and the second sensors 10B are provided in the regions 2D to which the palms of the hands are proximate. With this configuration, the first sensors 10A in the buttons 2A that the user operates with his (her) fingers Fg can preferably detect the fingerprints thereof, and the second sensors 10B in the regions 2D to which the palms of the hands are proximate can preferably detect the blood vessel patterns. The positions of the first sensors 10A and the second sensors 10B are not, however, limited thereto. FIG. 15 is a view illustrating another example of the keyboard. In the example of FIG. 15, the first sensors 10A are provided in buttons 2A1, and the second sensors 10B are provided in buttons 2A2. More specifically, the second sensors 10B are provided in the buttons 2A2 on the side farther from the user than the buttons 2A1 in which the first sensors 10A are provided, that is, upward in the direction Y. In the example of FIG. 15, the buttons 2A for inputting F and J are the buttons 2A1 in which the first sensors 10A are provided, and the buttons 2A for inputting R and U are the buttons 2A2 in which the second sensors 10B are provided. The buttons are, however, not limited thereto. In FIG. 15, the first sensors 10A are preferably sensors configured not to detect the blood vessel patterns but to detect the fingerprints, but may be sensors configured to detect both of the blood vessel patterns and the fingerprints.

As described above, the detection device 100 may have the configuration in which the first sensors 10A are provided in the buttons 2A1 on the side closer to the user than the button 2A2 and the second sensors 10B are provided in the buttons 2A2 on the side farther from the user than the buttons 2A1. When the blood vessel pattern is detected, a contact area of the finger Fg is preferably increased in comparison with the case of detecting the fingerprint. The buttons 2A2 are located on the farther side than the buttons 2A1 are. The user therefore tends to bring not his (her) fingertip but his (her) finger cushion into contact with the button 2A2 when operating the button 2A2, so that the contact area of the button 2A2 and the finger Fg is increased. Accordingly, such arrangement of the first sensors 10A and the second sensors 10B enables preferable detection of the blood vessel patterns and the fingerprints. The first sensor 10A and the second sensor 10B can be provided in both of the button 2A1 and the button 2A2 and be appropriately used alternately depending on a usage pattern of the input unit 1 by the user, the size of the hands of the user, or the like. The fingerprint or the blood vessel pattern may be detected not by the pressed button but by using a sensor 10 provided in a button adjacent to the pressed button. To be specific, when buttons 2A3 of "5" and "7" farther from the user than the buttons 2A2 of R and U are pressed, the fingerprint or the blood vessel pattern may be detected by driving the sensors provided in R, U, F, and J. The above description is merely an example, the size of the input unit 1, array of the keys of the input unit 1, and the keys in which the sensors are provided in accordance with the usage frequencies of the keys by the user, or the like can be appropriately modified. The sensors can also be provided in numeric keys when the usage frequency of the numeric keys are high. The embodiment has a characteristic in that a type of the biological information to be detected and a position of the biological information to be detected are made different depending on difference in the distance from the user.

The detection device 100 is not limited to the configuration in which the sensors 10 are provided in the keyboard 2 and may have the configuration in which the sensors 10 are provided in another input unit 1, for example, the mouse 4. The detection device 100 may have the configuration in which the sensors 10 are provided in both of the keyboard 2 and the mouse 4. That is to say, the detection device 100 may include the sensor 10 in at least one of the keyboard 2 and the mouse 4, which are the input unit 1.

Figure 16:
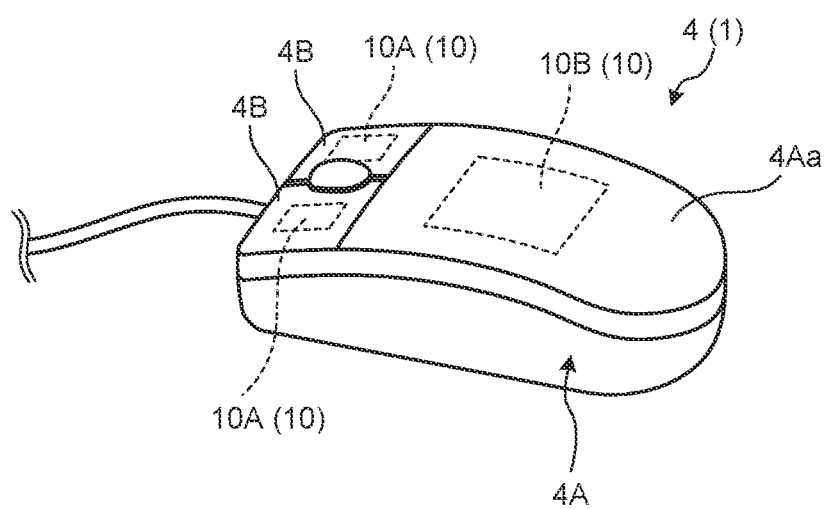
FIG. 16 is a view illustrating an example in which the sensors are provided in a mouse.

FIG. 16 is a view illustrating an example in which the sensors are provided in the mouse. As illustrated in FIG. 16, the mouse 4 includes a housing portion 4A and buttons 4B. The housing portion 4A is a main body of the mouse 4 and includes various devices therein. The buttons 4B are provided in a front-end portion of the housing portion 4A and receive click operation by the user. The user can move a cursor for display on the display unit 5 by holding and moving the housing portion 4A.

In the example of FIG. 16, the sensors 10 are provided in the mouse 4. More specifically, the first sensors 10A are provided in the buttons 4B, and the second sensor 10B is provided on a surface 4Aa of the housing portion 4A. The surface 4Aa of the housing portion 4A is provided on the rear-end side of the mouse 4 relative to the buttons 4B. Accordingly, when the user operates the mouse 4, the palm of the hand becomes proximate to the surface 4Aa of the housing portion 4A, and the fingers Fg of the user become proximate to the buttons 4B. The blood vessel pattern and the fingerprint can be preferably detected by providing the first sensors 10A in the buttons 4B that the user presses and providing the second sensor 10B in the housing portion 4A that is proximate to the palm of the hand of the user.

Figure 17:
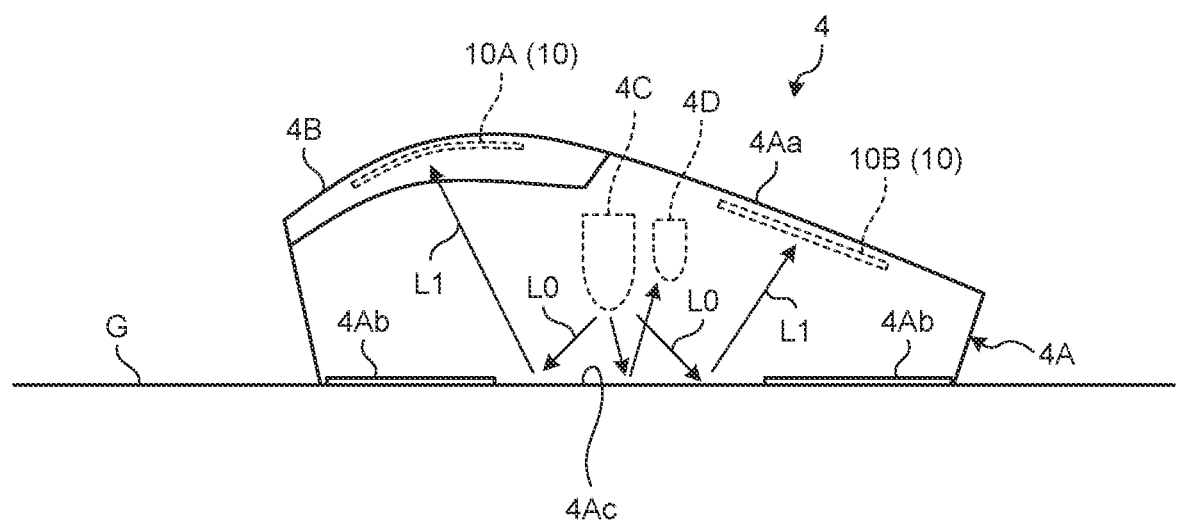
FIG. 17 is a schematic view illustrating an example of arrangement of the mouse, the sensors, and a light source.
Figure 18:
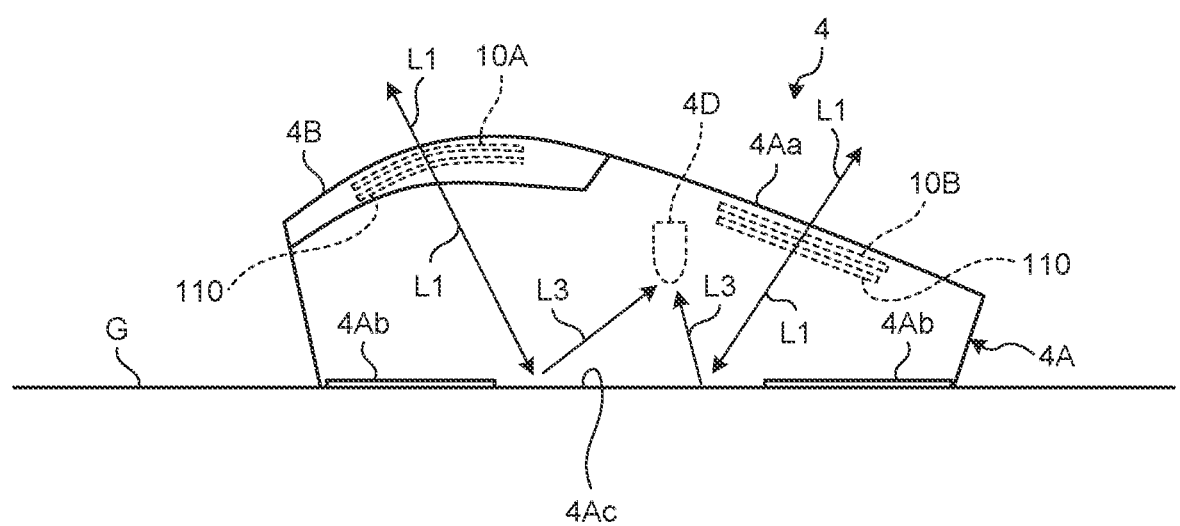
FIG. 18 is a schematic view illustrating another example of the arrangement of the mouse, the sensors, and the light sources.

When the mouse 4 is an optical mouse, the light source units of the sensors 10 and the light source unit of the mouse 4 can be made common to each other. FIG. 17 and FIG. 18 are schematic views illustrating examples of arrangement of the light sources of the mouse and the sensors. FIG. 17 illustrates an example in which the mouse 4 includes the light source unit and the sensors 10 include no light source unit. In the example of FIG. 17, the mouse 4 includes a light source unit 4C and a light receiver 4D in the housing portion 4A. In the example of FIG. 17, no light source unit 110 for the sensors 10 is provided. The mouse 4 has bottom surfaces 4Ab of the housing portion 4A that are brought into contact with a contact surface G, and an opening 4Ac for emitting light L0 from the light source unit 4C to the contact surface G is provided between the bottom surface 4Ab. The light L0 emitted from the light source unit 4C is reflected by the contact surface G after passing through the opening 4Ac and is emitted, as light L1, to the light receiver 4D. The movement amount and the movement direction of the mouse 4 are detected with the light L1 emitted to the light receiver 4D. The light L1 is emitted also to the sensors 10, and the sensors 10 can detect the biological information with the light L1.

FIG. 18 illustrates an example in which the mouse 4 includes no light source unit and the sensors 10 each include the light source unit 110. In the example of FIG. 18, the mouse 4 includes the light receiver 4D in the housing portion 4A. Light L1 emitted from the light source units 110 is emitted to the sensors 10, and the sensors 10 detect the biological information with the light L1. In the example of FIG. 18, the light source units 110 are configured such that the light L1 is emitted also to the contact surface G. Accordingly, the light L1 emitted from the light source units 110 is reflected by the contact surface G and is emitted, as light L3, to the light receiver 4D. The movement amount and the movement direction of the mouse 4 are detected with the light L3 emitted to the light receiver 4D. In the above-mentioned embodiment, when user authentication is performed by a terminal such as a personal computer, the user authentication can be performed while the user operates to input characters with the keyboard, and so on. Accordingly, a separate operation for the authentication therefore need not be performed. The user authentication can be performed over a period in which the user operates the keyboard or at predetermined intervals. When a plurality of users share the same detection device 100 (terminal), the authentication is needed every time the user is changed. In the embodiment, the detection device 100 recognizes the change of the user simultaneously with any input or an operation with the mouse by the user, so that the convenience of users is improved.

Second Embodiment

Next, a second embodiment is described. A detection device 100a according to the second embodiment is different from the first embodiment in a point that it is a device for financial transactions. Description of parts of the configuration in the second embodiment that are common to the configuration in the first embodiment is omitted.

Figure 19:
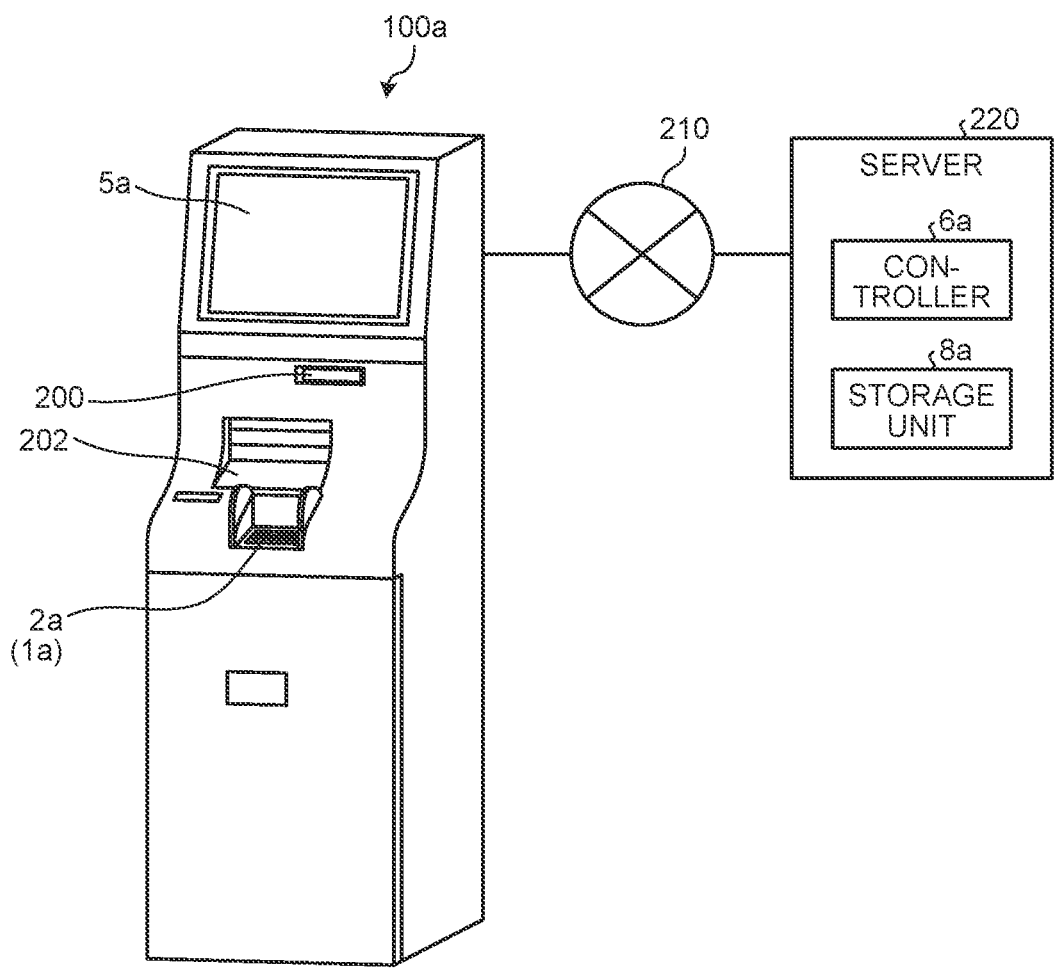
FIG. 19 is a schematic view of a detection device according to a second embodiment.

FIG. 19 is a schematic view of the detection device according to the second embodiment. As illustrated in FIG. 19, the detection device 100a is a device enabling deposit and withdrawal of cash. The detection device 100a is, for example, an automated teller machine (ATM) that is installed in financial institutions and the like and a multi-function machine that is installed in convenience stores and the like and handles cash. The detection device 100a includes a keyboard 2a as an input unit 1a, a display unit 5a, a card slot 200, and a bill processor 202. Although not illustrated in the drawing, the detection device 100a includes various types of circuits (the detection controller 11, the detector 40, and the like) for detecting biological information similarly to the detection device 100 in the first embodiment. The card slot 200 is configured to enable insertion and discharge of cards such as cash cards in transactions using the card. The card slot 200 discharges a receipt issued when the transaction is finished. The bill processor 202 receives and gives bills in deposit and withdrawal transactions.

The detection device 100a is coupled to a server 220 as an external apparatus via a network 210 and transmits and receives information to and from the server 220. The server 220 includes a controller 6a configured to execute similar functions to those of the controller 6 in the first embodiment and a storage unit 8a.

Figure 20:
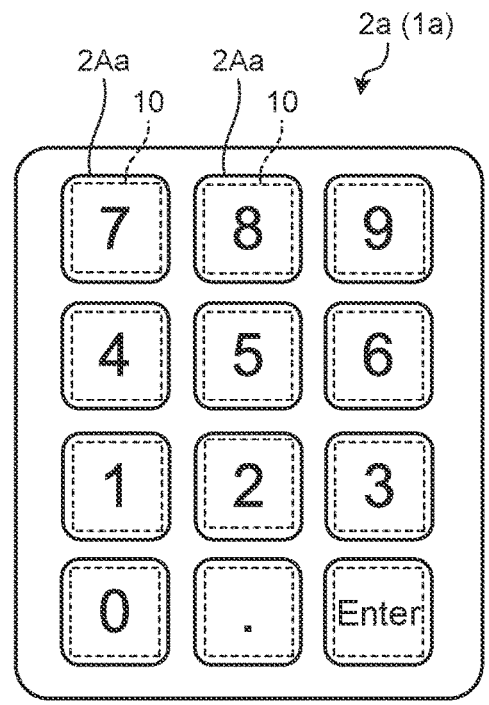
FIG. 20 is a view illustrating an example of a keyboard according to the second embodiment.

FIG. 20 is a view illustrating an example of the keyboard in the second embodiment. The keyboard 2a has a plurality of buttons 2Aa, and the sensors 10 are provided in the buttons 2Aa. The sensors 10 are preferably the first sensors 10A but may be the second sensors 10B.

The sensor 10 detects the biological information of the user when the user operates the button 2Aa. The biological information of the user that the sensor 10 has detected is transmitted to the server 220 via the network 210, and the controller 6a of the server 220 reads out reference biological information from the storage unit 8a and collates the reference biological information and the biological information of the user for authentication, similarly to the controller 6 in the first embodiment. When the reference biological information and the biological information of the user match, the controller 6a of the server 220 conveys information indicating such to the detection device 100a via the network 210. The detection device 100a starts a predetermined function (for example, a procedure of deposit and withdrawal). The detection device 100a starts the predetermined function and executes an operation (for example, numerical value input) assigned to the operated button 2Aa.

The detection device 100a is a device for the financial transactions, a device for control of room access, and the like as described above. When the detection device 100a is applied to a system that has a user interface such as a keyboard and performs predetermined processing by performing biological authentication of a user, the necessity of an operation only for the authentication is eliminated, thereby enabling reduction of labor and time for the authentication.

Third Embodiment

Next, a third embodiment is described. A detection device 100b according to the third embodiment is different from that of the first embodiment in positions at which the sensors 10 are provided, and is different from that of the first embodiment in a point that it is a touchscreen computer in which a display unit and an input unit are integrated with each other, that is, a what is called tablet terminal. Description of parts of the configuration in the third embodiment that are common to the configuration in the first embodiment is omitted.

Figure 21:
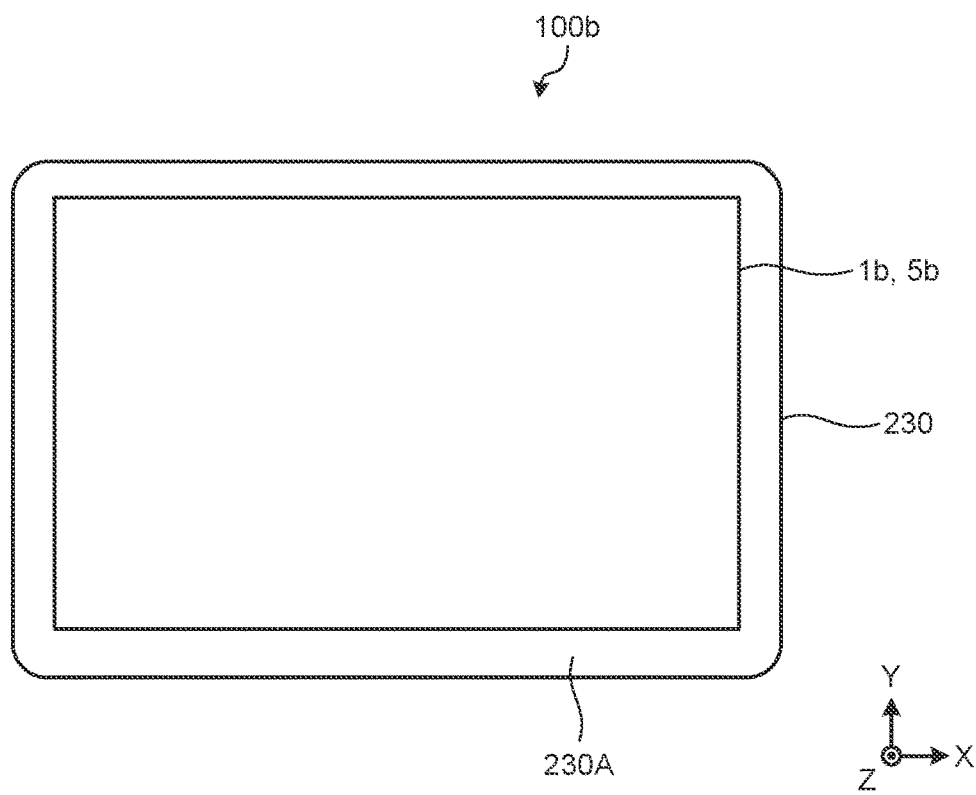
FIG. 21 is a schematic view of a detection device according to a third embodiment.

FIG. 21 to FIG. 24 are schematic views of the detection device according to the third embodiment. As illustrated in FIG. 21, the detection device 100b according to the third embodiment is a tablet computer in which a touchscreen panel including an input unit 1b and a display unit 5b that are stacked and are integrally configured is provided on a surface 230A of a housing portion 230. Although not illustrated in the drawings, the detection device 100b includes various types of circuits (the detection controller 11, the detector 40, and the like) for detecting biological information similarly to the detection device 100 in the first embodiment. The detection device 100b has a rectangular shape, the direction along the long side is a direction X, the direction along the short side is a direction Y, and the direction orthogonal to the surface 230A is a direction Z.

Figure 22:
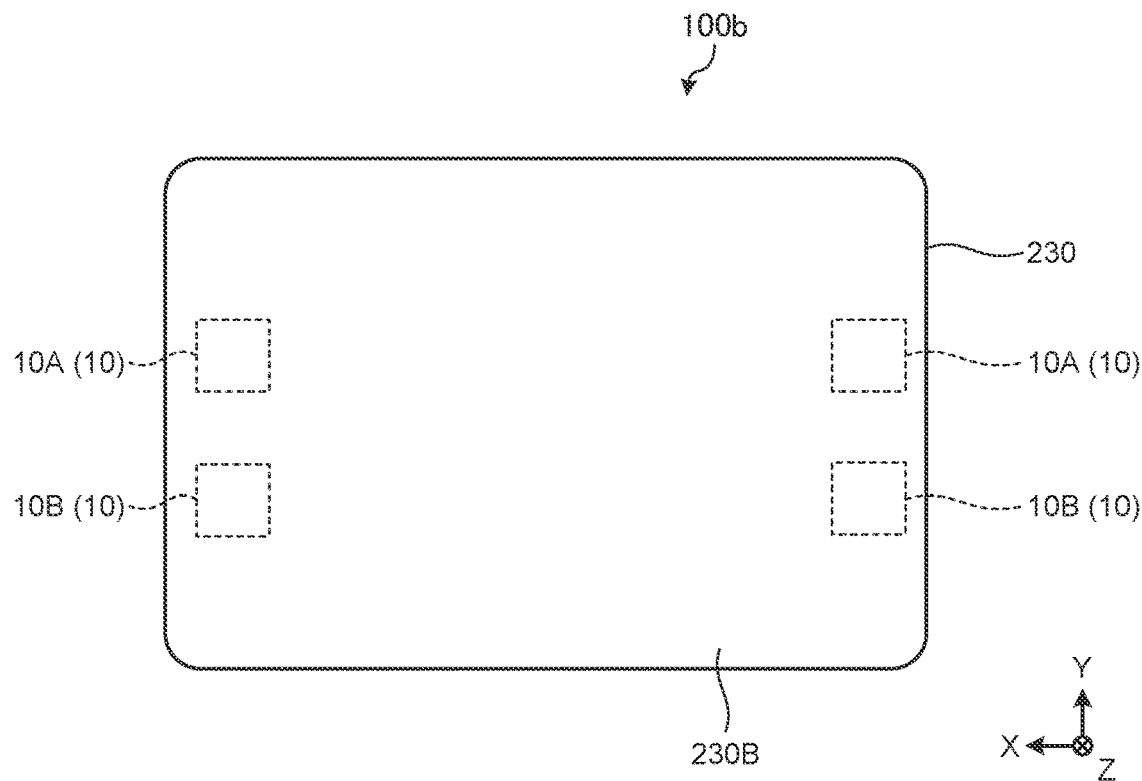
FIG. 22 is a schematic view of the detection device according to the third embodiment.
Figure 23:
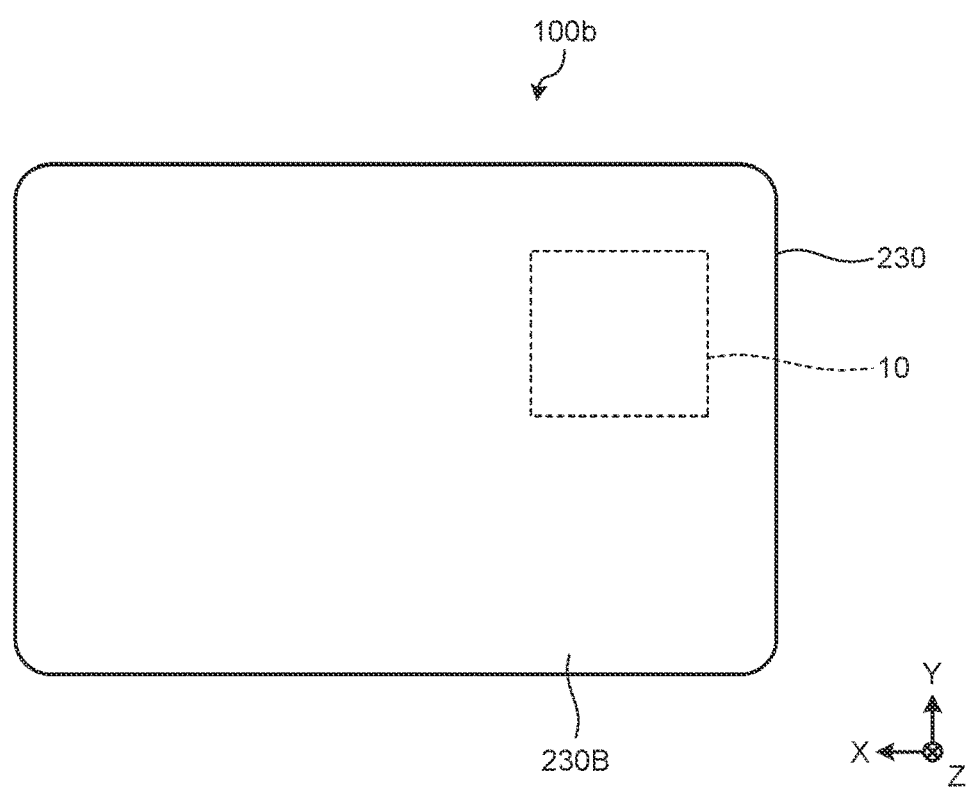
FIG. 23 is a schematic view of the detection device according to the third embodiment.
Figure 24:
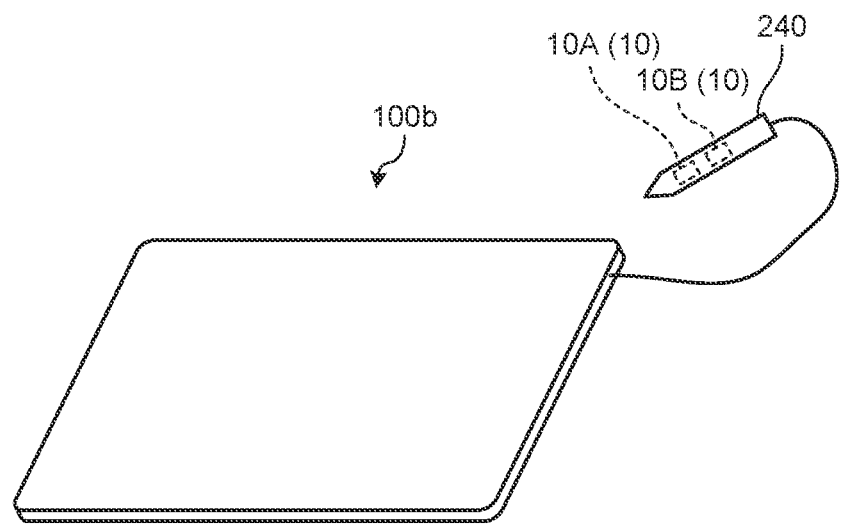
FIG. 24 is a schematic view of the detection device according to the third embodiment.

As illustrated in FIG. 22 and FIG. 23, the sensors 10 are provided on a back surface 230B of the housing portion 230 in the third embodiment. The back surface 230B is a surface on the opposite side to the surface 230A on which the touchscreen panel is provided. That is to say, the sensors 10 are provided in a region in which the input unit 1b and the display unit 5b are not provided. As illustrated in FIG. 22, for example, the sensors 10 may be provided on the back surface 230B on one end side and the other end side in the direction Y. A plurality of the sensors 10 may be provided on each of the one end side and the other end side of the back surface 230B in the direction Y, the sensors 10 being aligned along the direction X. One of the sensors 10 aligned along the direction X may be set as the first sensor 10A and another one may be set as the second sensor 10B. With such provision manner, the sensors 10 are provided at positions at which the user touches them when holding the detection device 100*b* and can detect the biological information of the user preferably. The positions at which the sensors 10 are provided are, however, not limited to those in the example of FIG. 22, and may be provided at a desired position on the back surface 230B, for example, as illustrated in FIG. 23. The sensors 10 are not limited to being provided on the back surface 230B and may be provided on side surfaces of the detection device 100*b* or in a frame region on the surface 230A in which the input unit 1*b* and the display unit 5*b* are not provided. A plurality of users can share a plurality of tablet terminals in applications such as merchandise management work. The embodiment enables correlations between the users and the terminals to be grasped all the time and enables efficient switching of a screen to be displayed on each terminal. The terminal that the user uses all the time can be provided with a support member in a shape fit to shapes of his (her) fingers on the side surfaces across the back surface of a terminal housing in order to enhance holding performance by his (her) hands. In this case, authentication can be made while the user is unaware of the sensor 10, by providing the sensor 10 in a portion of the support member that his (her) finger is brought into contact with. As illustrated in FIG. 24, the sensors 10 can be provided on the surface of a pen input unit 240 coupled to the detection device 100*b* as the tablet terminal. In this case, the first sensor 10A is preferably arranged on the side closer to the tip of the pen input unit 240 than the second sensor 10B. The tip of the pen input unit 240 is a portion at which a screen is touched by the pen input unit 240.

Other operation and effects provided by the aspects described in the embodiments that are obvious from the description of the present specification or at which those skilled in the art can appropriately arrive, should be interpreted to be provided by the present disclosure.

What is claimed is:
1. A detection device comprising:
an input device including an input device member and configured to receive an operation of a user, wherein the input device member includes a first input device member and a second input device member,
wherein the input device includes a sensor including a first sensor and a second sensor and configured to detect biological information of the user when the user operates the input device,
wherein the input device includes a light source unit including a first light source unit and a second light source unit,
wherein, in the input device, the first sensor is provided between the first input device member and the first light source unit,
wherein, in the input device, the second sensor is provided between the second input device member and the second light source unit,
wherein the first sensor and the second sensor include a plurality of optical sensors,
wherein the plurality of optical sensors of the first sensor include a first optical sensor and a second optical sensor exhibiting a sensitivity for different wavelength regions,
wherein the first optical sensor exhibits a first optical sensor sensitivity in a visible light wavelength region, and wherein the second optical sensor exhibits a second optical sensor sensitivity in a red wavelength region to an infrared wavelength region.

2. The detection device according to claim 1, further comprising a controller configured to determine whether a predetermined function is executed based on the acquired biological information of the user.

3. The detection device according to claim 2, wherein when the user inputs, to the input device, an operation of requesting execution of the predetermined function, the controller acquires, from the sensor, the biological information of the user in the operation of requesting the execution of the predetermined function, and determines whether the predetermined function is executed based on the acquired biological information of the user.

4. The detection device according to claim 2, wherein when the controller determines that the predetermined function is executed, the controller executes the operation assigned to the input device operated by the user in the detection of the biological information.

5. The detection device according to claim 1, wherein the sensor is provided in at least one of a keyboard and a mouse as the input device.

6. The detection device according to claim 1, wherein the first sensor is configured to detect a fingerprint of the user and the second sensor configured to detect a blood vessel pattern of the user.

7. The detection device according to claim 6, wherein the first sensor includes a semiconductor containing amorphous silicon, and the second sensor includes a semiconductor containing polysilicon.

8. The detection device according to claim 6, wherein the first sensor is provided on a side closer to the user than a keyboard as the input device, and the second sensor is provided on a side farther from the user than the first sensor is in the keyboard.

9. The detection device according to claim 6, wherein the first sensor is provided in a button that the user presses in a mouse as the input device, and the second sensor is provided in a housing portion that is proximate to a palm of a hand of the user in the mouse.

10. An authentication method of authenticating a user using a detection device including an input device configured to receive an operation of the user and a sensor provided in the input device and configured to detect biological information of the user when the user operates the input device, the authentication method comprising determining whether a predetermined function is executed based on the biological information of the user that the sensor has detected,
wherein the input device includes an input device member and configured to receive an operation of a user,
wherein the input device member includes a first input device member and a second input device member,
wherein the input device includes a sensor including a first sensor and a second sensor and configured to detect biological information of the user when the user operates the input device,
wherein the input device includes a light source unit including a first light source unit and a second light source unit, wherein, in the input device, the first sensor is provided between the first input device member and the first light source unit, and wherein, in the input device, the second sensor is provided between the second input device member and the second light source unit, wherein the first sensor and the second sensor include a plurality of optical sensors, and wherein the plurality of optical sensors of the first sensor include a first optical sensor and a second optical sensor exhibiting a sensitivity for different wavelength regions, wherein the first optical sensor exhibits a first optical sensor sensitivity in a visible light wavelength region, and wherein the second optical sensor exhibits a second optical sensor sensitivity in a red wavelength region to an infrared wavelength region.

11. The method according to claim 10, wherein the plurality of optical sensors, of the first sensor and the second sensor, are arranged in a matrix with a row-column configuration.

12. The method according to claim 10, wherein the second sensor has a larger area than the first sensor.

13. The detection device according to claim 1, wherein the plurality of optical sensors, of the first sensor and the second sensor, are arranged in a matrix with a row-column configuration.

14. The detection device according to claim 1, wherein the second sensor has a larger area than the first sensor.

* * * * *